United States Patent [19]

Critser et al.

[11] Patent Number: 5,691,133

[45] Date of Patent: Nov. 25, 1997

[54] METHOD TO QUICKLY ADD CRYOPROTECTANTS TO SPERM CELLS WHILE MAINTAINING VIABILITY

[75] Inventors: John K. Critser, Carmel; D. Y. Gao, Indianapolis, both of Ind.

[73] Assignee: Methodist Hospital of Indiana, Indianapolis, Ind.

[21] Appl. No.: 475,215

[22] Filed: Jun. 7, 1995

Related U.S. Application Data

[62] Division of Ser. No. 250,675, May 27, 1994, Pat. No. 5,595,866.
[51] Int. Cl.$^6$ .................................................. A01N 1/02
[52] U.S. Cl. .................................................. 435/2; 435/1.3
[58] Field of Search .................................. 435/1.3, 2

[56] References Cited

U.S. PATENT DOCUMENTS

| | | | |
|---|---|---|---|
| 4,429,542 | 2/1984 | Sankao et al. | 62/62 |
| 4,464,337 | 8/1984 | Zelman | 422/41 |
| 4,965,186 | 10/1990 | Grischenko et al. | 435/2 |
| 4,980,277 | 12/1990 | Junnila | 435/2 |
| 5,026,342 | 6/1991 | Hammerstedt et al. | 600/35 |
| 5,261,870 | 11/1993 | Hammerstedt et al. | 600/35 |

OTHER PUBLICATIONS

Fertility & Sterility, vol. 14, No. 1, issued 1963, J.K. Sherman, "Improved Methods of Preservation of Human Spermatozoa by Freezing and Freeze-Drying", pp. 49–64.
Acta Vet. Scand., vol. 32, No. 4, issued 1991, C.O. Bwanga, "Cryopreservation of Boar Sperm", pp. 431–453.
Cryobiology, vol. 26, issued 1989, Fiser et al., "The Effect of Glycerol-Related Osmotic Changes on Post-Thaw Motility and Acrosomal Integrity of Ram Spermotozoa", pp. 64–69.
Cryobiology, vol. 29, issued 1992, Gao et al., "Glycerol Permeability of Human Spermatozoa and its Activation Energy", pp. 657–667.

Biology of Reproduction, vol. 49, issued 1993, Gao et al., "Hyperosmotic Tolerance of Human Spermatozoa: Separate Effects on Glycerol, Sodium Chloride, and Sucrose on Spermolysis", pp. 112–113.
The American Fertility Society and Methodist Hospital of Indiana, Inc. in cooperation with the Reproductive Biology Special Interest Group, Critser et al., "Advanced Hands-On Workshop on Cryopreservation of Spermatozoa and Embryos", Postgraduate course at Methodist Hospital of Indiana, Indianapolis, IN on 11–13 Jun. 1993, mailed to participants no earlier than 01 Jun. 1993.
O. Kedem & A. Katchalsky, "Thermodynamic Analysis of the Permeability of Biological Membranes to Non-Electrolytes", vol. 27 (1958), Biochimica Et Biophysica ACTA.
Junying Du, F.W. Kleinhans, P. Mazur and J.K. Critser, Osmotic Behavior of Human Spermatozoa Studied by EPR, Cryo-Letters 14, 285–294 (1993).
E.E. Noiles, P. Mazur, P.F. Watson, F.W. Kleinhans, and J. K. Critser, "Determination of Water Permeability Coefficient for Human Spermatozoa and its Activation Energy", Biology of Reproduction, 48, 99–109 (1993).

Primary Examiner—Sandra E. Saucier
Attorney, Agent, or Firm—Woodard, Emhardt, Naughton, Moriarty & McNett

[57] ABSTRACT

A mathematical model to optimize protocols for the addition or removal of cryoprotectant to or from sperm cells. This disclosure describes the use of four equations to predict optimal protocols to add or remove cryoprotectant to or from sperm cells. The equations particularly require experimentally found date, specific to a species of sperm, regarding the osmotic tolerance of sperm cells, where osmotic tolerance refers to the sperm cells ability to shrink or swell to various changes in osmolality without injury. The equations further require the cryoprotectant permeability coefficient and the water permeability coefficient of the particular sperm cells' plasma membrane. Also disclosed are two particularly preferred methods to add or remove cryoprotectant to or from sperm. These preferred methods are Fixed-Volume-Step addition/removal of cryoprotectant or Fixed-Molarity-Step addition/removal of cryoprotectant.

12 Claims, 21 Drawing Sheets

■ : 250 mOsm
○ : 230 mOsm
● : 190 mOsm
▽ : 143 mOsm
▼ : 114 mOsm
□ : 90 mOsm a: 0.5M glycerol
b: 1M glycerol
c: 1.5M glycerol
d: 2M glycerol 1: ORIGINAL SPERM IN 1M GLYCEROL
2: ONE-STEP RETURNED TO ISOTONIC MEDIUM
3: 8-STEP RETURNED TO ISOTONIC MEDIUM (FIXED-MOLARITY)
4: 8-STEP RETURNED TO ISOTONIC MEDIUM (FIXED VOLUME)
5: 2-STEP RETURNED TO ISOTONIC MEDIUM USING SUCROSE AS AN OSMOTIC BUFFER.

METHOD TO QUICKLY ADD CRYOPROTECTANTS TO SPERM CELLS WHILE MAINTAINING VIABILITY

This application is a divisional of application Ser. No. 08/250,675, filed May 27, 1994, now U.S. Pat. No. 5,595,866.

This invention was made with Government support under Grant No. HD02549-01 awarded by the National Institute of Health. The Government has certain rights in the invention.

BACKGROUND OF THE INVENTION

Fresh sperm is viable for a relatively short period of time, typically only from about one to eight days. However, it is often advantageous to utilize sperm long after it has been collected, sometimes several months or even years later. Various methods, principally freezing, are employed to preserve sperm for these relatively longer periods of time. Freezing sperm permits, for example, a domestic animal breeder to maintain stocks of valuable sperm for use when necessary, enables the inexpensive transport of such stocks, and ultimately permits genetically superior males to inseminate a larger number of females. Beyond livestock, artificial insemination is also used in the human context for various medical and health reasons.

The preservation of sperm has proven to be quite troublesome. The survivability of viable cells using prior art freezing methods is often quite low. Freezing conditions are relatively harsh and thermal shock or other phenomena such as ice crystal formation often kill the sperm. Therefore, maximizing the viability of thawed cells has been the goal of many researchers.

The prior art discloses various methods for improving the survivability of frozen sperm. U.S. Pat. No. 4,007,087 (to Ericsson) discloses a sperm fractionation and storage method which claims to increase the percentage of motile sperm that survive frozen storage. Ericsson discloses a method whereby motile sperm are separated from non-motile, defective or dead sperm. The fraction containing the motile sperm is then frozen. Ericsson reports that his method increases the fertility of a sperm sample by enhancing the environmental (the ratio of total sperm to motile sperm) and viability (progressiveness of motility of the motile sperm) factors effecting the fertility of a sample, but his method does not improve the population (motile sperm count) factor which is possibly the most critical.

U.S. Pat. No. 3,791,384 (to Richter et al.) discloses a method for deep freezing and thawing boar sperm which includes inactivating the fresh sperm by means of an inactivating solution that includes dextrose, dihydrate of ethlenedinitrotetra-acetic acid, sodium citrate and sodium hydrogencarbonate. Richter reports that inactivation of the sperm gives them a greater power of resistance to freezing.

U.S. Pat. No. 4,429,542 (to Sakao et al.), U.S. Pat. No. 4,487,033 (to Sakao et al.), U.S. Pat. No. 3,893,308 (to Barkay et al.) and U.S. Pat. No. 4,480,682 (to Kameta et al.) all disclose different freezing methods which claim to improve the fertility of sperm samples. In all of these methods, the temperature of sperm in solution is lowered by various means which attempt to reduce the thermal shock and increase the survivability of the viable sperm and ova present. Most of these methods are, however, complex, cumbersome and expensive to utilize. Other freezing methods are also used including the "Sherman" method of rapid freezing in liquid nitrogen vapors (Sherman, J. K., Improved Methods of Preservation of Human Spermatozoa by Freezing and Freeze Drying, Fertil. Steril., 14:49–64 (1963), and the "Behrman-Sanada" method of gradual freezing (Behrman et al. Meterologous and Humologus Inseminations with Human Semen Frozen and Stored in a Liquid Nitrogen Refrigerator., Fertil. Steril. 17:457–466 (1966).

A disadvantage of the aforementioned methods resides in that low-temperature preservation of sperm is accompanied by the ice crystallization process. The ice crystallization process is retarded by the use of a cryoprotectant; however, the influence of the cryoprotectant on reducing ice crystallization is offset by the negative effects of the cryoprotectant on the ejaculate. Addition of a cryoprotectant typically results in injury to the cytoplasmic membrane of the sperm, because the addition leads to powerful osmotic shifts. The osmotic shifts cause partial denaturation of the protein molecules and disorientation of the cell organelles. In addition, if the sperm have prolonged exposure to a high concentration of cryoprotectant before freezing, there is also concern that the cryoprotectant will be toxic to the sperm.

SUMMARY OF THE INVENTION

One aspect of this invention is a method to predict appropriated protocols to remove cryoprotectant from sperm cells based on the sperm cells' upper volume limit, the sperm cell membrane's cryoprotectant permeability coefficient, and the sperm cell membrane's water permeability coefficient.

A second aspect of this invention is to stepwise apply the predetermined lower concentrations of cryoprotectant to the sperm of a particular species to remove cryoprotectant from the sperm.

A third aspect of this invention is sperm that has had cryoprotectant removed in accordance with the methods described in this invention.

A fourth aspect of this invention is a method to predict appropriate protocols to add cryoprotectant to sperm cells based on the sperm cells' lower volume limit, the sperm cell membrane's cryoprotectant permeability coefficient, and the sperm cell membrane's water permeability coefficient.

A fifth aspect of this invention is to stepwise apply the predetermined higher concentrations of cryoprotectant to the sperm of a particular species to add cryoprotectant to the sperm.

A sixth aspect of this invention is sperm containing cryoprotectant, where the cryoprotectant was added to the sperm in accordance with the methods described in this specification.

Furthermore, this invention has the following advantages over the empirical approach of the prior art:

(1) the method is usable for other cryoprotectants besides the commonly used glycerol, (2) the method is usable to predict protocols for differing concentrations of cryoprotectants, (3) the use of modeling is faster and cheaper than empirical methods (basically trial and error). And, much information can be determined before actual use, like: (a) minimum time interval between cryoprotectant addition/removal steps (b) maximum amount of cryoprotectant or diluent used for each step, and (c) the least number of steps required to prevent osmotic injury. This information is otherwise not readily available especially if one changes sperm species, type of cryoprotectant, cryoprotectant concentration, or even temperature of the cryoprotectant's use.

Within this specification, the term "predetermined concentration" refers to a concentration that has been calculated not to exceed or not to substantially exceed the sperm cells' upper volume limit (CPA removal) or lower volume limit (CPA addition) using the permeability coefficients of water and cryoprotectant through the sperm's membrane.

Within this specification, the term "contacting" refers to the physical contact that allows cryoprotectant and water to pass through the sperm cells' plasma membrane.

Within this specification, the term "volumetric excursion" refers to the sperm cells' volume substantially shrinking or substantially swelling beyond limits that have been predetermined to cause a predetermined percentage of sperm cells to be injured.

BRIEF DESCRIPTION OF THE DRAWINGS

In the accompanying drawings, forming a part of this specification.

DESCRIPTION OF THE PREFERRED EMBODIMENT

Figure 1:
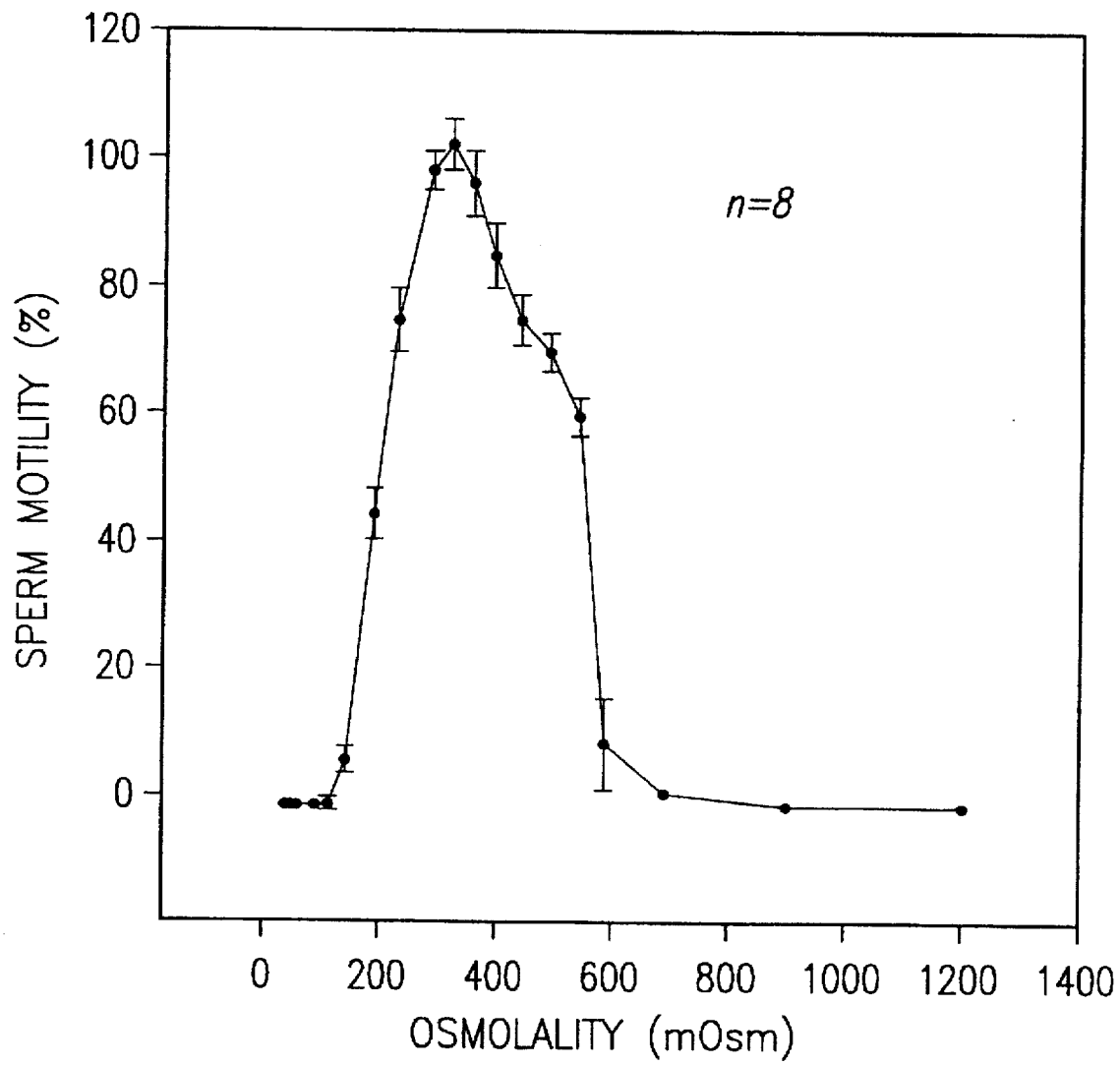
FIGS. 1 to 4 are graphical portrayals of examples of injury to sperm cells as a function of osmolality.
Figure 1A:
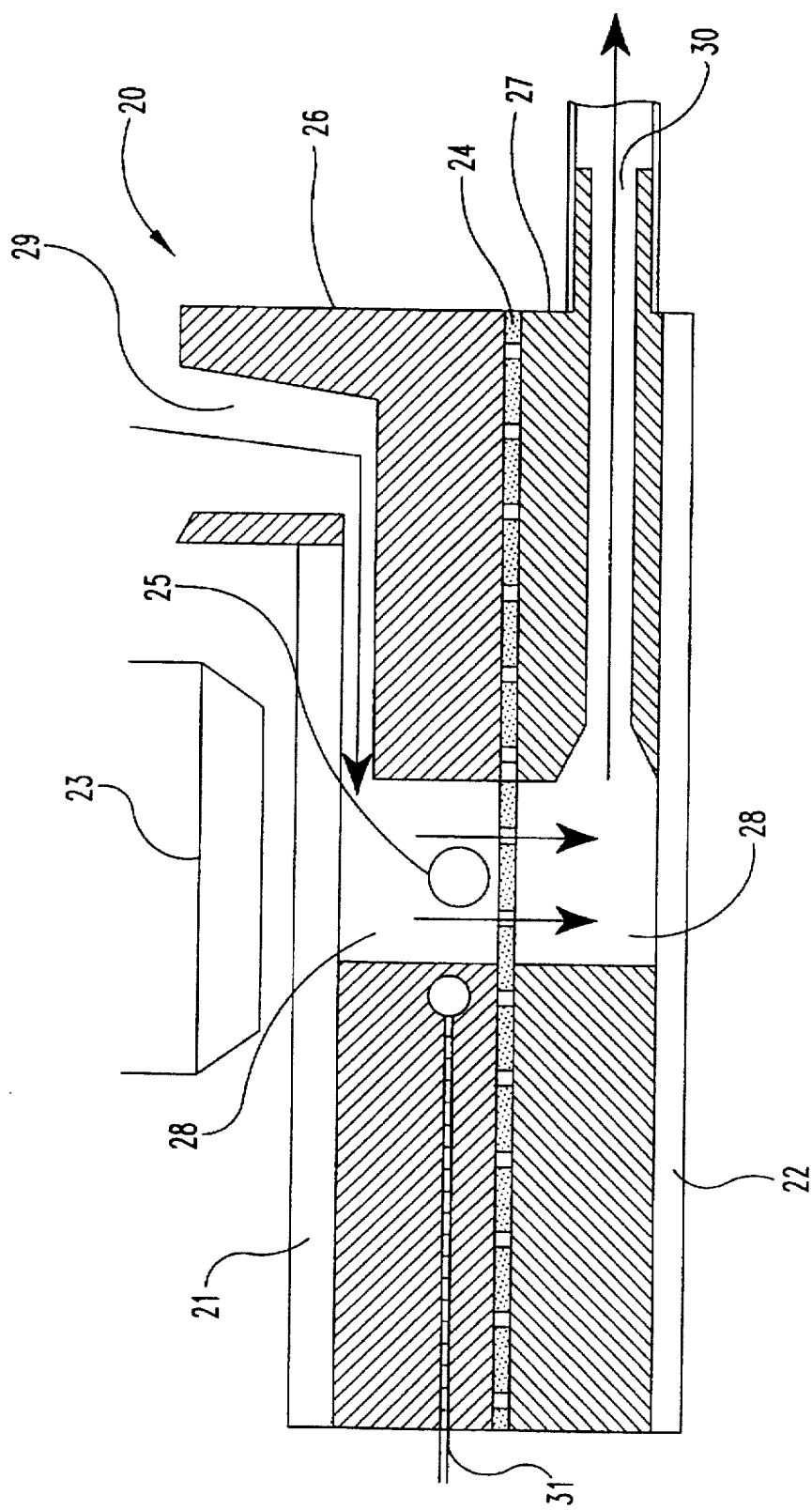

Specific language is used to describe several embodiments of this invention to promote an understanding of the invention and its principles. It must be understood that no limitation of the scope of this invention is intended by using this specific language. Any alteration and further modification of the described method or any application of the principles of this invention are also intended that normally occur to one skilled in this art.

Osmotic stress is known to cause injury to biological cells such as sperm. Sperm experience this stress during the passage of cryoprotective agent (CPA) across the sperm membrane, both into or out of the sperm cells. The stress is typically caused by sperm cells shrinking or swelling beyond or below their volumetric limit during the passage of CPA through the sperm membrane. The present inventive method optimizes CPA addition or CPA removal by reducing this stress. For presentation purposes, this invention is described in three aspects. The first aspect concerns finding upper and lower volumetric limits of a particular species of sperm. The second aspect concerns predicting conditions to transport water and CPA through the sperm membrane based on such volumetric limits. The third aspect concerns applying the predicted conditions.

Finding Upper and Lower Volumetric Limits of Sperm

A first aspect of this invention concerns evaluating sperm for their volumetric limits or their "osmotic tolerance." Osmotic tolerance refers to the sperm's ability to withstand shrinking or swelling without injury. This evaluation determines the sperm's volumetric limits to swelling and shrinking before a user-defined percentage of the sperm lose their viability, e.g. lose their motility or lyse. Typical user-defined percentages of viability loss may be as high as 50%, or as low as 20%, 10%, 5% or even less than 1%.

A preferred procedure to determine osmotic tolerance is to expose the sperm to various anisosmotic solutions and noting the degree of cell lysing or motility loss that occurs upon exposure to a particular osmotic pressure and noting the time period of exposure. Once osmotic limits are found, the sperm cell volumes can then be calculated. Typical anisosmotic solutions might range from 40 to 1200 mOsm (milliosmols); however, the exact anisosmotic solutions may vary with the species of sperm and any user preferences. Typical anisosmotic exposure times might range from as little as 5 seconds to as long as 30 minutes, and ultimately depend upon user-defined preference and other factors discussed near the end of this specification. After exposure, the sperm cell sample is evaluated for the degree that sperm in the sample lose their viability, typically measured by their loss of motility or degree of lysing. Both the exposure step and the evaluation step are repeated over a range of anisosmotic solutions so as to experimentally correlate the degree of cell injury with osmotic pressure and time of exposure.

One preferred procedure to assess sperm cell viability (here, measuring sperm cell plasma membrane integrity) utilizes dual flourescent staining and flow cytometric analysis as disclosed by Garner in *Assessment of Spermatozoal Function Using Dual Fluorescent Staining and Flow Cytometric Analysis*, Biol. Reprod. 34, 127–138, 1986, which is hereby incorporated into this specification by reference. Propidium iodide (PI) is a bright red, nucleic acid-specific fluorophore available from the Sigma Chemical Co. PI permeates poorly into sperm with intact plasma membranes, however, it readily diffuses into sperm having damaged membranes and stains the DNA red. 6-Carboxyfluoroscein diacetate (CFDA) is a membrane-permeable compound which is also available from the Sigma Chemical Co. CFDA penetrates into the sperm and is hydrolyzed by intracellular esterase to 6-carboxy fluoroscein (CF). CF is a bright green, membrane-impermeable fluorophore. Thus, when CFDA is added into the sperm suspension, membrane-intact spermatozoa fluoresce bright green. Membrane integrity is then tested by exposing a sperm sample to a solution containing both PI and CFDA and performing flow cytometric analysis upon the sperm sample after contact and basing the analysis upon the amount and/or location of the color present.

Another method to determine Sperm cell viability (here, the loss of sperm cell motility) utilizes computer assisted semen analysis (CASA) using CELLSOFT™ (for example version 3.2/C available from CRYOResources™, LTD). CASA is a widely recognized method to determine sperm cell motility, having been used for many years and is Well within the skill of this art to use.

Once the osmotic limits are determined, the Boyle van't Hoff relationship is utilized to find the upper and lower volume limits of the sperm cells. This equation is a simple linear relationship:

$$V_w = V_i(M_i/M) + V_a$$

where $V_w$ is the volume of a sperm cell at osmolality M, $V_i$ is the volume of an osmotically active sperm cell at the isotonic osmolality, $M_i$, and $V_a$ is the volume of an osmotically inactive sperm cell. This equation is discussed in *Osmotic Behavior of Human Spermatozoa Studied by EPR,* by Du, Kleinhans, Mazur, and Critser, in Cryo-Letters, 14, 285–294 (1993), the disclosure of which is hereby incorporated into this specification by reference.

Calculating Appropriate Conditions to Transport Water and CPA Through the Sperm Membrane The formulation of coupled, passive membrane transport can be modeled in the present invention by first-order, non-linear equations. These equations are discussed in *Thermodynamic Analysis of the Permeability of Bilogical Membranes to Non-Electrolytes*, by Kedem and Katchalsky, in Biochimica et Biophysica ACTA, Vol. 27 (1958), the disclosure of which is hereby incorporated by reference into this specification.

These equations respectively describe total membrane volume flux ($J_v$) and transmembrane permeable solute flux ($J_{CPA}$). Assuming the solution consists of a single permeable solute (here, CPA) and other impermeable solutes, the mathematical equations are:

$$J_V = 1/A_c \, dV(t)/dt \quad \text{Equation 1}$$
$$= -L_p\{(C^e_{salt} - C^i_{salt}) + \sigma(C^e_{CPA} - C^i_{CPA})\}$$

and, $$J_{CPA} = 1/A_c \, dN_{CPA}/dt \quad \text{Equation 2}$$
$$= \bar{C}_{CPA}(1-\sigma)J_v + P_{CPA}(C^e_{CPA} - C^i_{CPA})RT$$

where $J_v$=total volume flux, V=sperm volume, t=time, N=mole number of solute, $A_c$=sperm surface area, $L_p$=water permeability coefficient of the sperm membrane, C=concentration of solute, $J_{CPA}$=CPA flux across the cell membrane, superscript e=extracellular, superscript i=intracellular, $\bar{C}_{CPA}$=average CPA concentration of extracellular and intracellular concentrations. Furthermore, R=gas constant, T=absolute temperature, $P_{CPA}$=CPA permeability coefficient of the sperm membrane, and σ=the reflection coefficient of the particular CPA. The reflection coefficient is generally specific to a particular cryoprotectant and represents the opposing actions of water and cryoprotectant moving in opposite directions through the sperm cell membrane. Typically it is assumed to be 1. For example, using glycerol as the CPA, a value of 0.7 to 1 has only insignificant effect on the predictions found using this model. However, it must be remembered that its exact value is dependent on the cryoprotectant utilized and is a point where the user may fine tune the model for their particular use.

The mathematical models for intracellular concentrations of impermeable solute (salt) and permeable solute (CPA) are:

$$C_{salt}^i(t) = C_{salt}^{e,0}\{(V(0) - V_b - \bar{V}_{CPA}N_{CPA}^{i,0})/(V(t) - V_b - \bar{V}_{CPA}N_{CPA}^i(t))\} \quad \text{Equation 3}$$

$$C_{CPA}^i(t) = [N_{CPA}^i(t)]/[V(t) - V_b - \bar{V}_{CPA}N_{CPA}^i(t)] \quad \text{Equation 4}$$

where $V_b$=osmotically-inactive cell volume, $\bar{V}_{CPA}$=partial mole volume of CPA, N=mole number, and 0=initial condition (t=0). Initial conditions for V(0) $C_{salt}^i(0)$ $C_{CPA}^i(0)$, $N_{CPA}^i(0)$ are known based upon the actual conditions present. When using these models in computer simulation, it can be assumed that (a) extracellular concentrations of permeating and nonpermeating agents are constant, and that (b) the mixture of solutions during the CPA addition and removal are instantaneous.

The kinetics and effects of various schemes of CPA addition or removal to a solution of sperm are evaluated using equations 1 to 4. Once a particular concentration of cryoprotectant is chosen, the equations (1–4) are utilized in iterative fashion to determine whether the sperm cells upper or lower volume limit has been exceeded or significantly exceeded. The placement of these equations into computer code to perform this calculation is within the skill of this art.

Examples of the physical values for human sperm needed are shown in Table 1. Similar values for other species of sperm are within the skill in the art to obtain. For example, the permeability coefficient of the cryoprotective agent can be determined using procedures as disclosed in *Glycerol Permeability of Human Spermatozoa and its Activation Energy*, by Gao, Mazur, Kleinhans, Watson, Noiles, and Critser, Cryobiology 29, 657–667, the disclosure of which is hereby incorporated by reference into this specification; or, the permeability coefficient of water can be determined using procedures as disclosed in *Determination of Water Permeability Coefficient for Human Spermatozoa and its Activation Energy*, by Noiles, Mazur, Watson, Kleinhans, and Critser; Biology of Reproduction 48, 99–109 (1993) the disclosure of which is also hereby incorporated by reference into this specification.

In review, the user of this invention first determines the concentration of cryoprotectant desired to be added or removed from a sperm cell suspension. Afterward, equations 1 to 4 are utilized in iterative fashion, typically with the aid of a computer, to determine whether the addition of this concentration of cryoprotectant causes the sperm cells to shrink or swell beyond their predetermined lower or upper volumetric limit. Examples of schemes to add cryoprotectant to sperm of given initial concentration include: (1) the multi-step addition or removal of CPA in constant volumes, (2) the multi-step addition or removal of CPA in constant molarity changes, or (3) the multi-step addition or removal of CPA in the presence of a non-permeating solute as an osmotic buffer.

Fixed-Volume-Step (FVS) Addition of CPA

The addition of CPA medium to a sperm suspension, in fixed volumes, is calculated with the following equation:

$$V_f = [(M_f V_o)/(M_o - M_f)]1/n \quad \text{Equation 5}$$

where $M_f$=final CPA concentration in a sperm suspension (molarity), $M_o$=CPA concentration in original CPA medium (molarity), n=total number of stages, i=ith step addition (In this specification ith step or kth step refers to one of the total steps undertaken, for example ith (kth) could be the 4th step of 8 total steps), $V_o$=original volume of isotonic sperm suspension, and $v_f$=volume of CPA medium added into the sperm suspension at each step of a multi-step addition.

Fixed-Molarity-Step (FMS) Addition

The addition of CPA medium to a sperm suspension, in fixed molarity increases, is calculated with the following equation:

$$V_i = (M_f V_o n M_o)/[(nM_o - iM_f)(nM_o - (i-1)M_f)] \text{ for } i=1 \text{ to } n \quad \text{Equation 6}$$

or $$V_i = [1/(\lambda n - i)]V_{i-1}^* \quad \text{Equation 7}$$

where $$V_{i-1}^* = V_o + \Sigma V_k \text{ for } k=1 \text{ to } i-1 \quad \text{Equation 8}$$

and where $$\lambda = M_o/M_f \quad \text{Equation 9}$$

and $$\Delta M = M_o/n \quad \text{Equation 10}$$

where $M_f$=final CPA concentration in cell suspension (molarity), $M_o$=CPA concentration in original CPA medium (molarity), n=total number of steps, i=ith step addition, $V_o$=original volume of isotonic sperm suspension (ml), $\Delta M$=increment of CPA molarity in sperm suspension after each step of CPA addition, $V_{i-1}{}^*$=the total volume of cell suspension before the ith step addition, $v_i$=volume of CPA medium added into the sperm suspension at the ith step.

Fixed-Volume-Step (FVS) Removal

Given the initial volume of the sperm suspension ($V_o$) and the initial concentration of the CPA ($M_o$), the total volume of isotonic solution required to dilute CPA concentration from $M_o$ to $M_s$ is calculated by the following:

$$V = V_o\{(M_o/M_s)-1)\} \quad \text{Equation 11}$$

Using the FVS scheme, the volume of isotonic solution added into sperm suspension at the ith step during the first n−1 steps (n steps in total) is calculated as follows:

$$V_i = V/(n-1) = [V_o/(n-1)][(M_o/M_s)-1] \quad \text{Equation 12}$$

where $M_s$=CPA concentration in sperm suspension (molarity) after n−1 step dilutions, $M_o$=CPA concentration in initial sperm suspension (molarity), n=total number of steps, i=the ith step addition, $V_o$=original volume of sperm suspension (ml) and $V_i$=volume of isotonic solution added into the sperm suspension at the ith step. After n−1 steps of adding isotonic solution into the sperm suspension, the diluted sperm suspension is centrifuged, for example, at 400 g for 5–7 minutes., and then the sperm pellet is resuspended in isotonic solution to make the last (nth) step dilution.

Fixed-Molarity-Step (FMS) Dilution

In this scheme the CPA concentration in the sperm suspension is stepwise diluted by adding isotonic solution and decreasing the molarity of the CPA in fixed steps. The following equation is used to calculate the volume of isotonic solution added into the sperm suspension at the ith step during the first n−1 steps (n steps in total)

$$\Delta M = M_o/n \quad \text{Equation 13}$$

$$V_i = [1/(n-1)]V_{i-1}{}^*, \ i=1 \ to \ n-1 \quad \text{Equation 14}$$

$$V_{i-1}{}^* = V_o + \Sigma V_k, \ k=1 \ to \ i-1 \quad \text{Equation 15}$$

where $\Delta m$=decrement of CPA molarity in the sperm after each step addition of the isotonic solution, $M_o$=CPA concentration in initial sperm suspension (molarity), n=total number of steps, i=ith step addition, $V_o$=original volume of sperm suspension, $V_{i-1}{}^*$=the total volume of sperm suspension before the ith step addition, and $V_i$=volume of isotonic solution added into sperm suspension at ith step. After n−1 steps of the addition, the CPA concentration in the sperm is diluted to $\Delta M = M_o/n$. Then the sperm will be transferred to isotonic conditions, which makes the last (the nth) step removal of CPA.

EXAMPLES

Example 1

Finding Upper and Lower Volumetric Limits

The human semen used in this example was obtained by masterbation from healthy donors after at least two days of sexual abstinence. The samples were allowed to liquefy in an incubator for 1 hour, at 37° C., in high humidity, and in 5% $CO_2$ and 95% air. A swim-up procedure was performed to separate motile sperm from immotile sperm. The motile sperm suspensions were centrifuged at 400×g for 7 minutes and then were resuspended in isotonic TL-Hepes medium, that is, HEPES-buffered TALP medium (286–290 mOsm) supplemented with Pyruvate (0.01 mg/ml) and BSA (4 mg/ml), at a cell concentration of $1 \times 10^9$ sperm/ml.

Sperm motility was measured by computer assisted semen analysis (CASA) using CELLSOFT™, version 3.2/C. CASA was performed before, during, and after the anisosmotic exposures of the sperm samples. All experiments were conducted at 22° C.

Plasma membrane integrity was analyzed by placing five µl of CFDA (suspended in 0.25 mg/ml of DMSO) and 5 µl of PI (suspended in 1 mg/ml $H_2O$) solutions into 0.5 ml of a particular sperm suspension. The cells with CFDA staining and without PI staining were considered as intact cells. An analytical determination of the percentage of intact sperm remaining in each sample was then made. A total of $1 \times 10^5$ spermatozoa per treatment were analyzed using a FACSTAR PLUS™ flow cytometer.

The FACSTAR PLUS™ flow cytometer settings were:

(1) Gates were set using forward and 90° light scatter signals at acquisition to exclude debris and aggregates.

(2) Instrument alignment was performed daily with fluorescent microbead standards to standardize sensitivity and setup.

(3) Photomultiplier settings were adjusted for spectral overlap with individually stained cells.

(4) Excitation was at 488 nm from a 4 Watt Argon laser operating at 200 mWatts. Fluorescein emission intensity was measured using a 530/30 bandpass filter, and PI intensity using a 630/22 bandpass filter.

Anisosmotic solutions ranging from 40 to 1200 mOsm were prepared using only non-permeating solutes and water. Hyposmotic solutions were made by diluting TL-HEPES medium with reagent grade water. Hyperosmotic solutions were prepared by adding sucrose or NaCl to the TL-HEPES medium. (Sucrose, NaCl, and the solutes in the TL-HEPES medium were considered to be membrane-impermeable compounds.)

Ten µl of the isotonic cell suspension (286–290 mOsm, $1 \times 10^9$ sperm/ml) were mixed with 150 µl of each anisosmotic solution. After CASA, and a time period from 5 seconds up to 30 minutes, the sperm in each anisosmotic solution were ultimately returned to isotonic condition by adding 150 µl of isotonic TL-HEPES medium to 10 µl of each anisosmotic sperm suspension. (The percentage of sperm which maintained motility or plasma membrane integrity after each treatment was normalized to that of sperm in untreated control samples for the following discussion.)

The normalized percentage of motile sperm in anisosmotic solutions (containing nonpermeable solutes only) ranging from 40 to 1200 mOsm is shown in FIG. 1. It was observed under microscopy (a) that a part of sperm lost their motility immediately after being exposed to the anisotonic solutions, (b) that sperm motility was reduced with either an increase or decrease of osmolality, and (c) that almost all sperm lost motility immediately after being exposed to any solution with an osmolality over 600 mOsm or below 120 mOsm.

Figure 2:
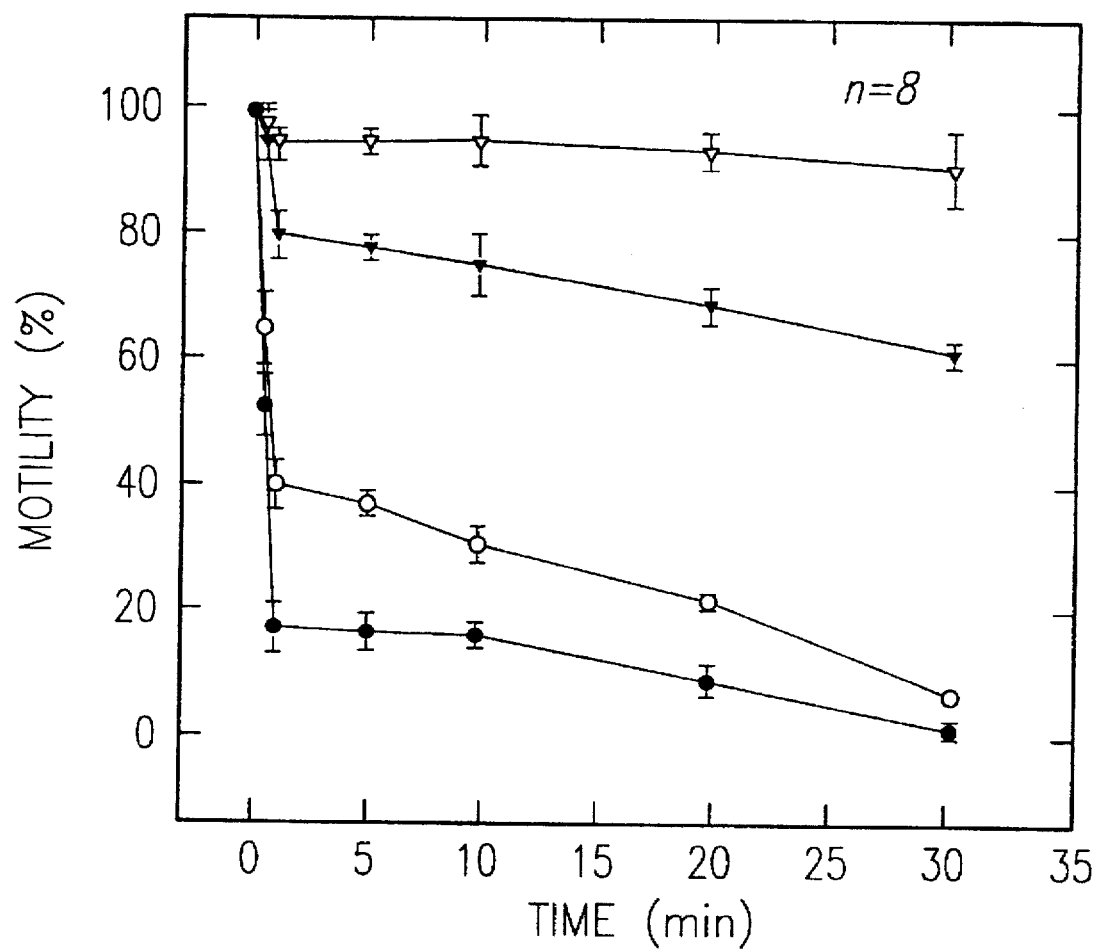
Figure 2A:
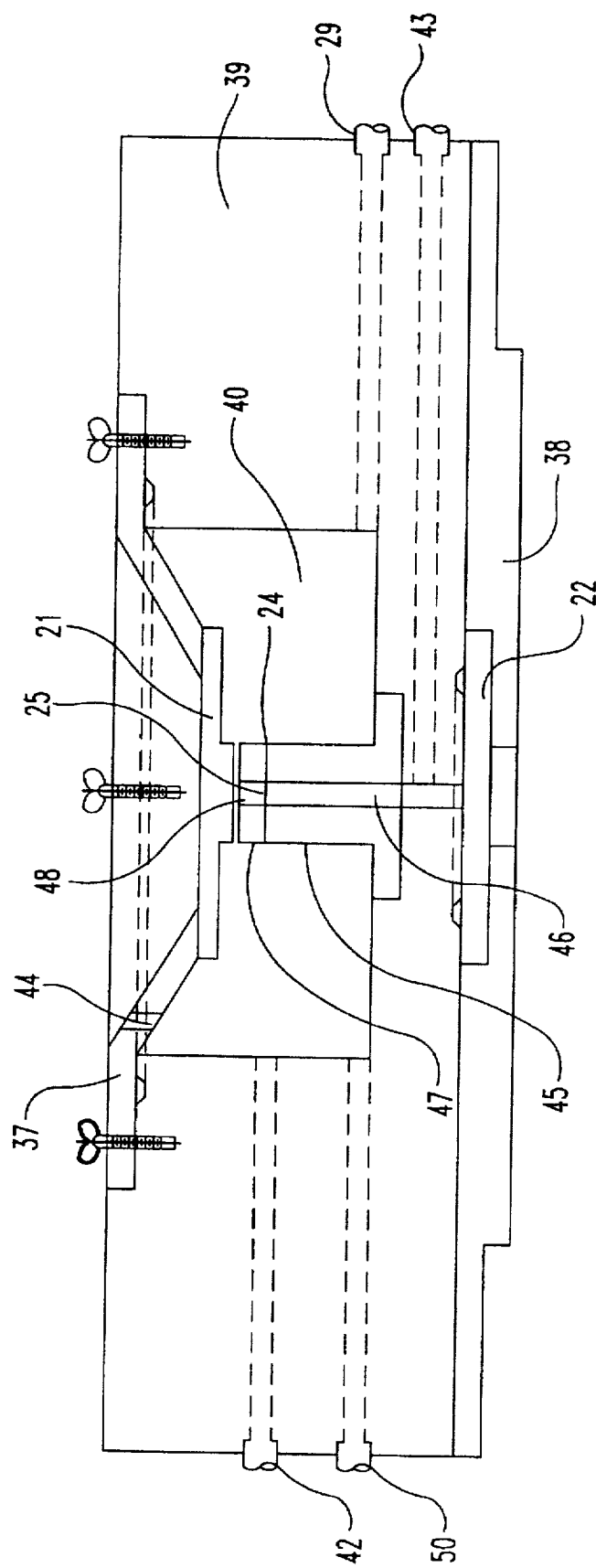
Figure 3:
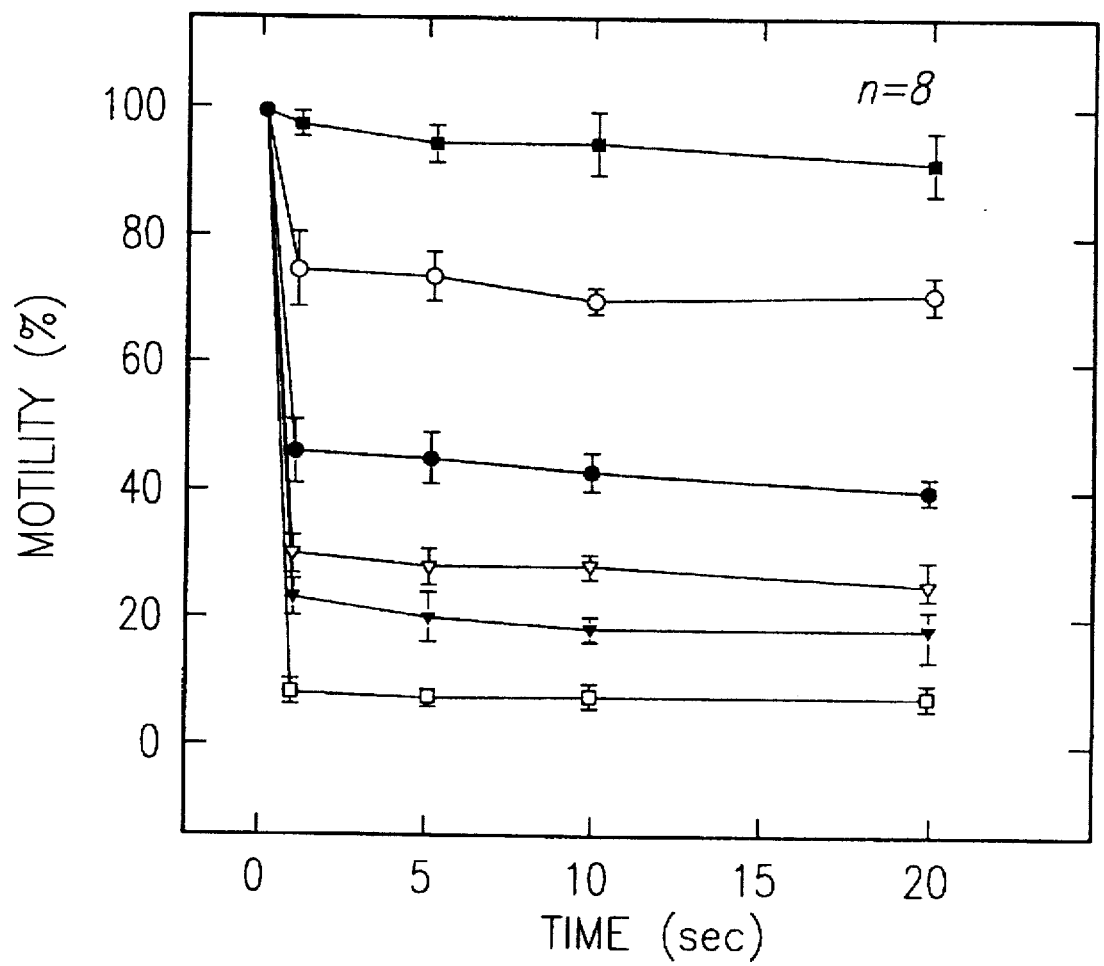
Figure 3A:
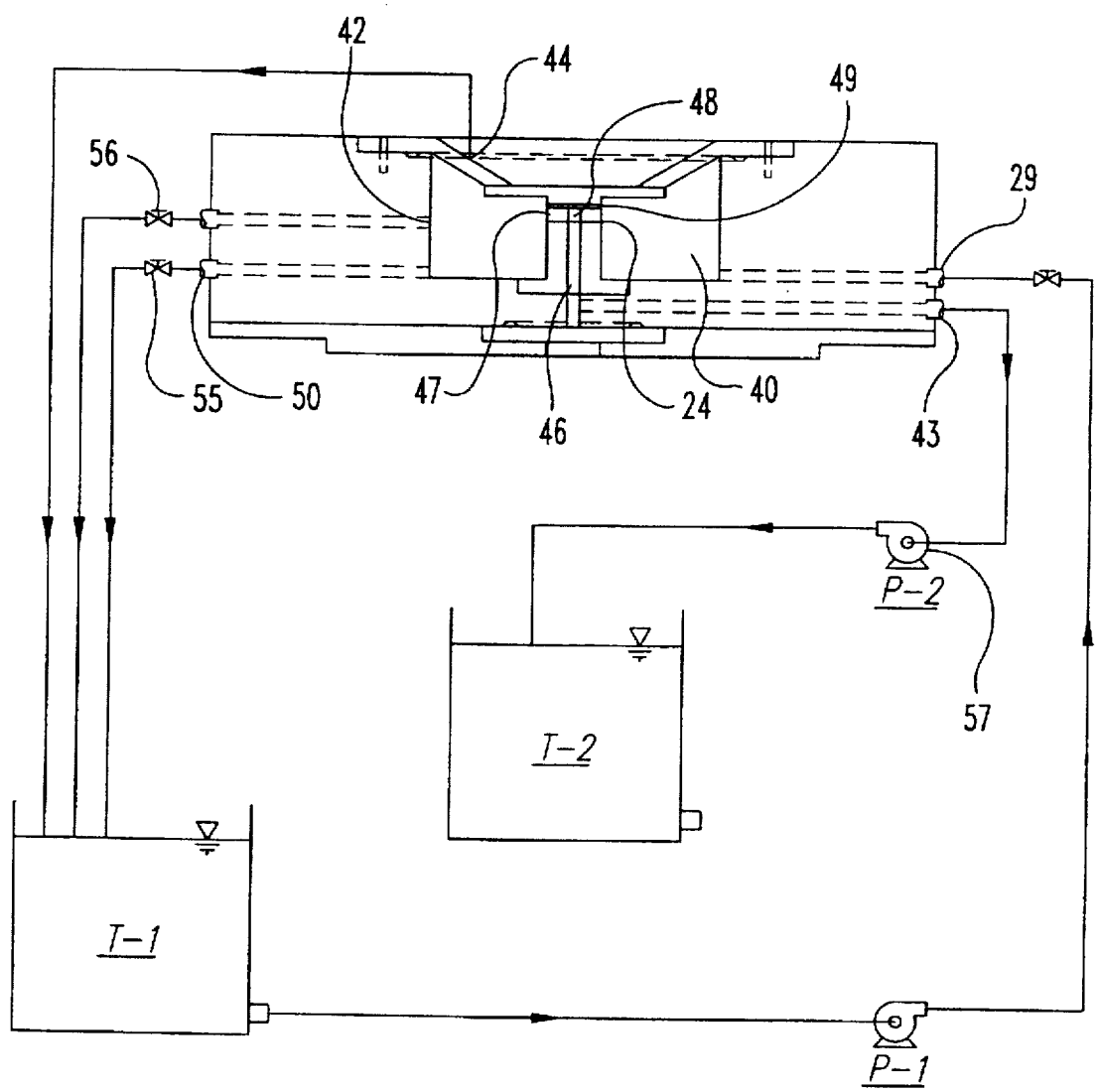
Figure 4:
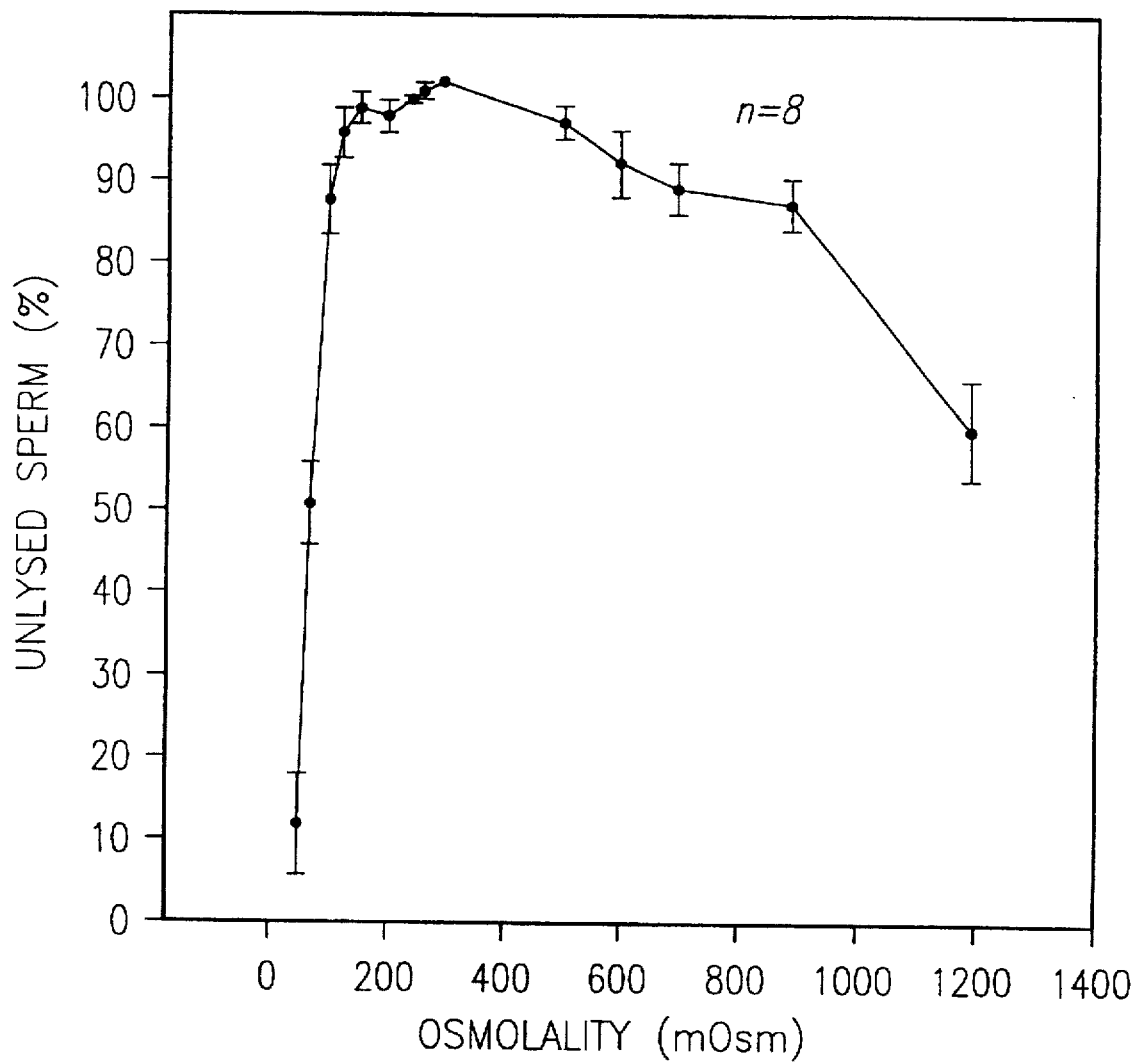

FIGS. 2 and 3 show post-hyperosmotic and post-hyposmotic sperm motility as a function of osmolality and as a function of time of sperm exposure to the anisosmotic conditions. FIG. 4 shows that the plasma membrane integrity of the human sperm returned to isosmotic conditions after a 10-minute exposure to the anisosmotic conditions. From FIGS. 2 to 4, motility was found to be substantially more sensitive to anisotonic conditions than membrane integrity, and motility was found to be more sensitive to hypotonic conditions than to hypertonic conditions. For example, exposure to 190 mOsm rendered half the sperm non-motile (FIG. 3), whereas half the sperm lost membrane integrity only when the osmolality was lowered to near 60 mOsm (FIG. 4). Most of the motility loss in hyposmotic conditions occurred within 1 sec (FIG. 3), with a slow further decline over the next 20 sec. The first apparent loss in motility in sperm, where sperm were exposed to hypertonic conditions and returned to isotonic conditions, occurred at 600 mOsm (FIG. 2), with more than half being rendered non-motile by a 1 minutes exposure to 900 mOsm. There was again a slow further decrease in motility as the exposure time was extended.

Figure 5:
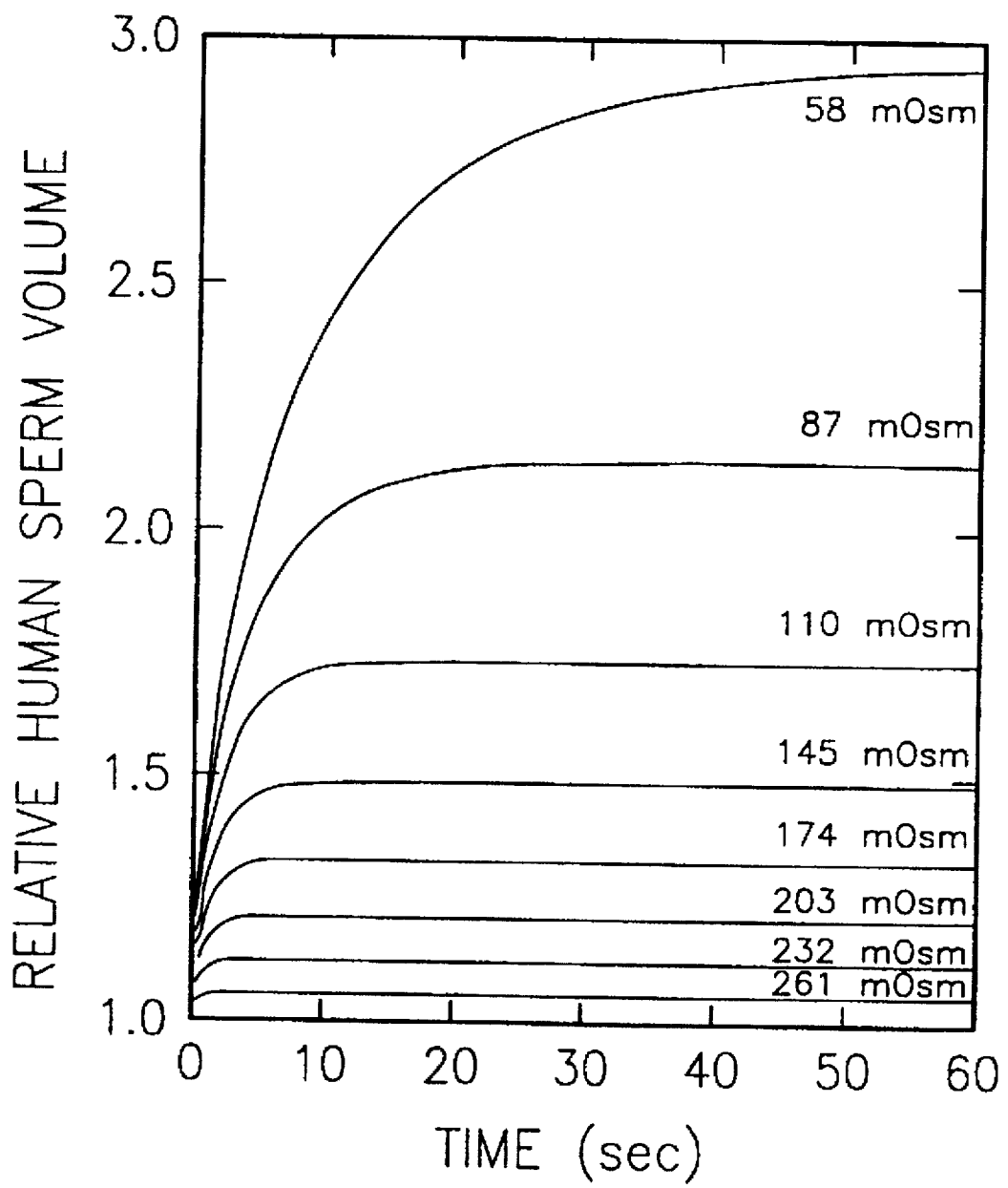
FIGS. 5 to 8 are graphical portrayals of examples of calculated sperm volumes as a function of osmolality.
Figure 6:
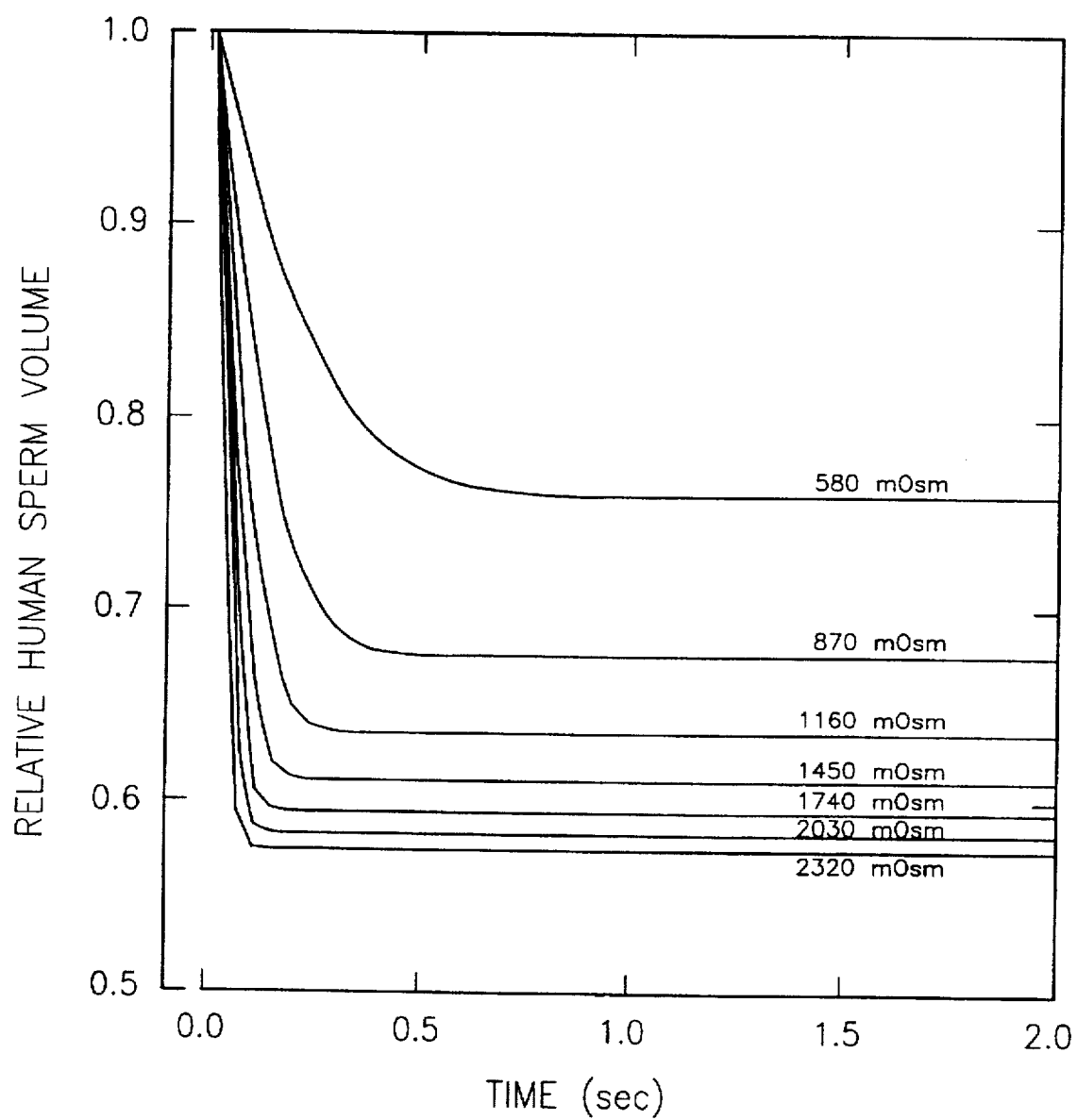

FIGS. 5 and 6 respectively show the predicted volume changes of the sperm after exposure to hypo- and hyper-osmotic solutions using equations 1 to 4 on this system. Based on the calculations performed, it was expected that human sperm shrank or swelled to osmotic equilibration volumes within one second (for shrinking) to a few seconds (for swelling).

In sum, from FIGS. 2 and 3, it was found that a part of the sperm irreversibly lost motility when returned to isotonic conditions after having been exposed to anisosmotic conditions. This post-anisosmotic motility loss was shown to be a function of both the exposure time and the osmolality. Since the anisosmotic solutions used contained only membrane-impermeable solutes, it was expected that sperm shrank or swelled when exposed to hyperosmotic or hyposmotic solutions. The shrunken or swollen sperm recovered their original volumes when returned to isotonic conditions.

A similar pattern, with the sperm's volume first shrinking or swelling and then recovering, takes place during the CPA addition or removal process from the sperm. Generally, when a cell is placed in a solution that is hyperosmotic with respect to the permeating solute (e.g. glycerol) but isotonic with respect to the impermeable salts, it first shrinks because of the osmotic efflux of intracellular water and then increases in volume as the solute (e.g. glycerol) permeates and as water concomitantly reenters the cell. When cells with CPA are exposed to an isotonic solution, they will swell because of osmotic influx of extracellular water and then decrease in volume as the CPA diffuses out of the sperm and as water concomitantly moves out.

Figure 7:
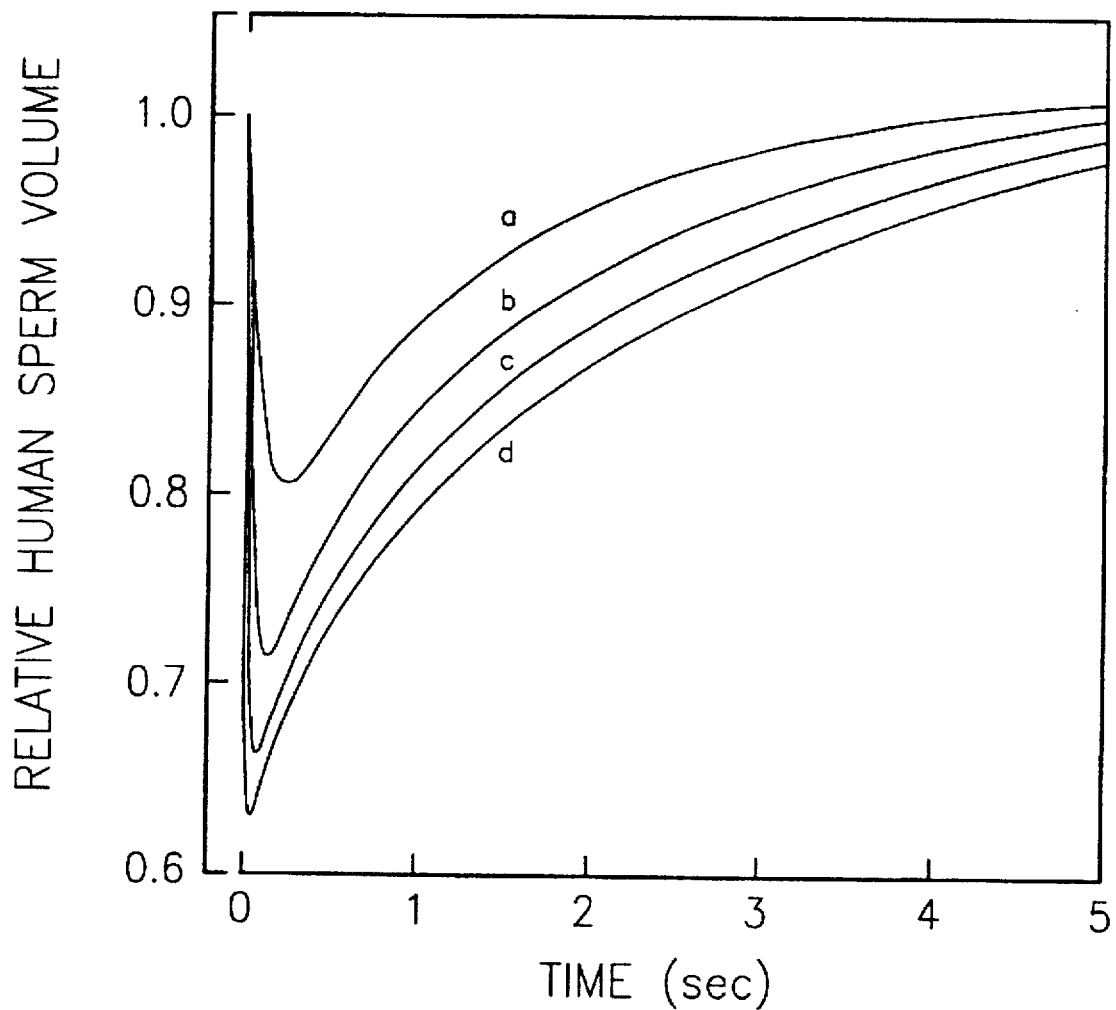
Figure 8:
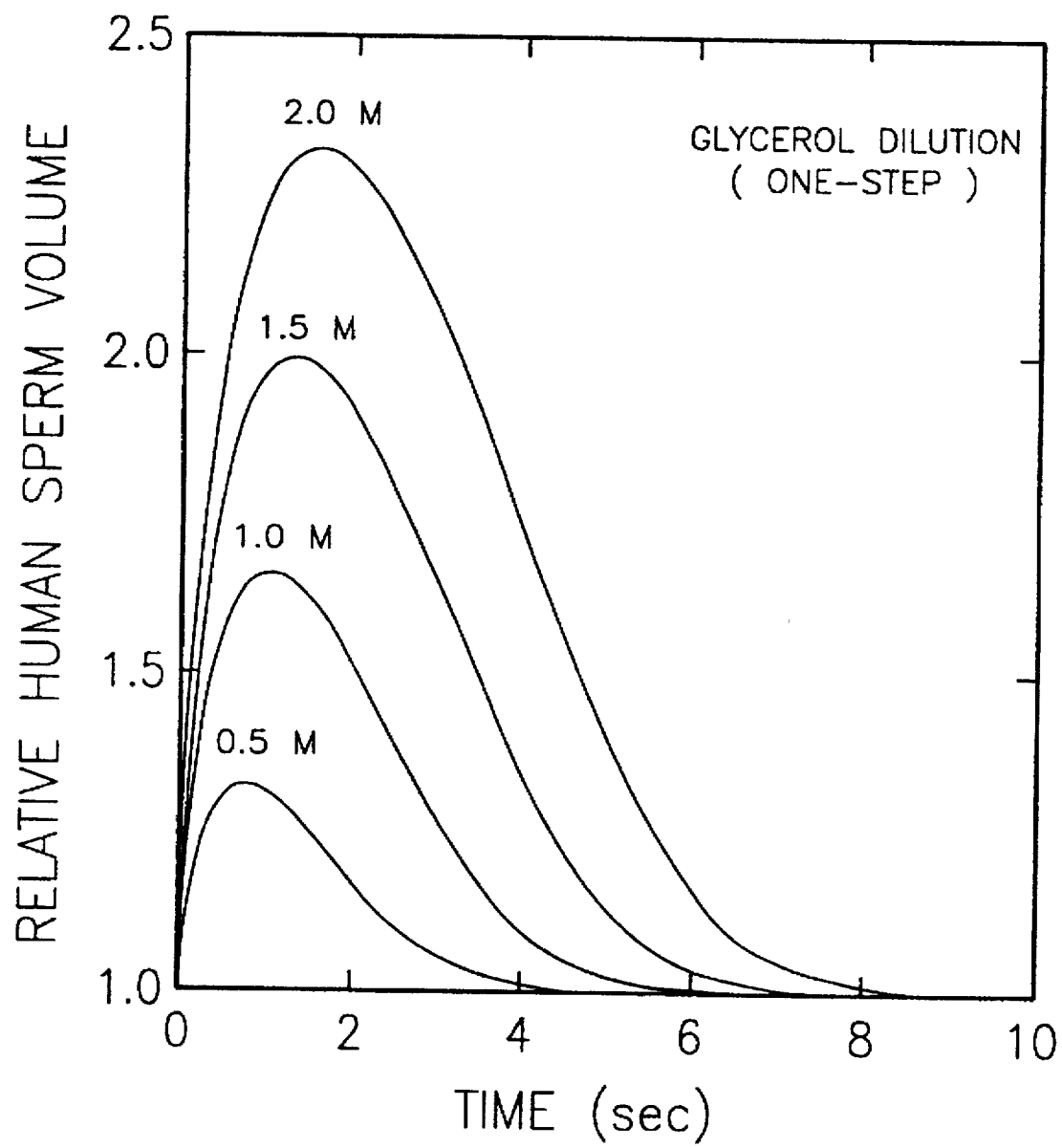

The sperm's volume changes during a 1-step addition and a 1-step removal of 9.5-2M glycerol were calculated from computer simulation and are respectively shown in FIGS. 7 and 8. The higher the glycerol concentration, the longer the time period taken for the sperm volume recovery. However, typically it takes but a few seconds for human sperm to achieve their osmotic equilibration volumes. This means that the sperm experience the shrunken or swollen states for only an order of seconds during the addition or removal of glycerol. Therefore, the information concerning post-anisosmotic tolerance of the sperm returned to isotonic conditions after a short time exposure (an order of seconds) to the anisosmotic conditions is particularly important for designing optimal CPA addition/removal procedures to prevent sperm osmotic injury.

Figure 9:
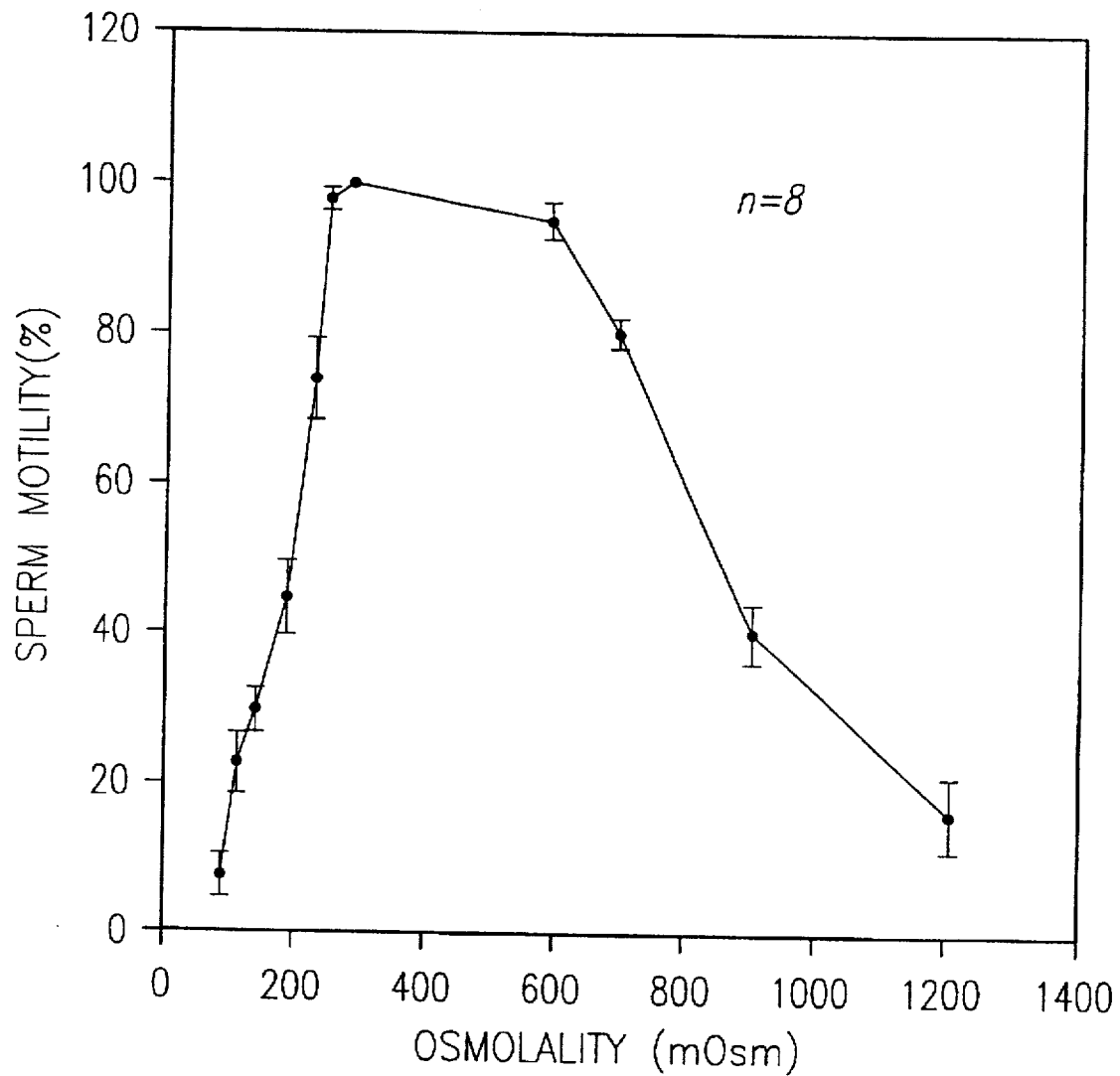
FIG. 9 is a graphical portrayal of an example of injury to sperm cells as a function of osmolality.

This information is obtained from FIGS. 2 and 3 which show the post-anisosmotic motility loss of the sperm as a function of the osmolality and the exposure time. Based on FIGS. 2 and 3, the post-anisosmotic motility of human sperm with a short time exposure (an order of seconds) to anisosmotic conditions is summarized in FIG. 9 as a function of osmolality. To obtain a high (over 95%) motility recovery, the highest and lowest osmolalities which the human sperm can tolerate for a short time were found to be close to 600 mOsm and 240 mOsm, respectively (FIG. 9). Using these two osmolalities, the corresponding cell volumes were calculated using equation 3 or estimated from FIGS. 5 and 6 to be approximately 0.75 (75%) and 1.1 (110%) times of isotonic human sperm volume, (values from FIGS. 5 and 6 being derived from the van't Hoff equation). This indicates that the sperm can only swell or shrink in a relative narrow range for a relative short time to avoid the motility loss. Again, the determined sperm volume limits are:

Upper Volume Limit (UVL): 1.1×isotonic sperm volume

Lower Volume Limit (LVL): 0.75×isotonic sperm volume

Table 1. Known characteristics of human spermatozoa
Surface area (A) ... 120 um$^2$
Volume (V) ... 34 um$^3$
Osmotically inactive volume (Vb) ... 16.6 um$^3$
Water permeability coefficient (Lp) ... 2.16 um/minutes/atm (22° C.)
Glycerol permeability coefficient(Ps) 1.1×10$^{-3}$ cm/minutes (22° C.)
(Similar values for sperm of different species are within the the skill in the art to obtain.)

Example 2

Prediction of Optimal Conditions for Glycerol Addition or Removal

The kinetics of water and glycerol transport across the sperm membrane were modeled using standard computing techniques that are well within the skill of the art of this invention and using Equations 1 to 4. Two preferred schemes of CPA addition, Fixed-Volume-Step (FVS) and Fixed-Molarity-Step (FMS), were analyzed in this regard and are presented below.

Figure 10:
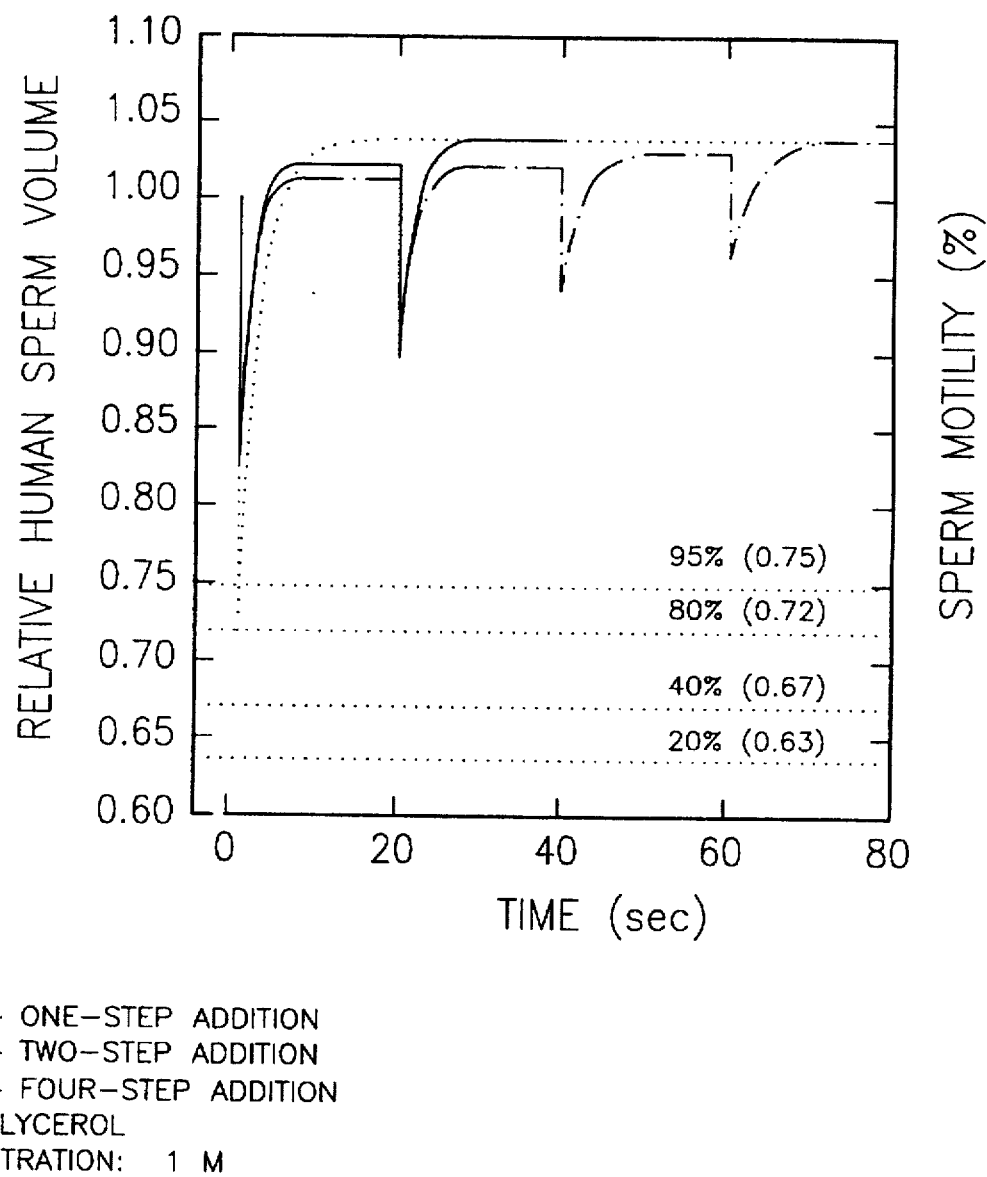
FIGS. 10 to 14 are graphical portrayals of examples of calculated sperm volumes as a function of osmolality.

Referring to FIG. 10, there is shown the calculated sperm volume change arising during a one-step, a two-step, and a four-step addition of glycerol to achieve a final 1M glycerol concentration at 22° C. using an FMS addition.

Figure 11:
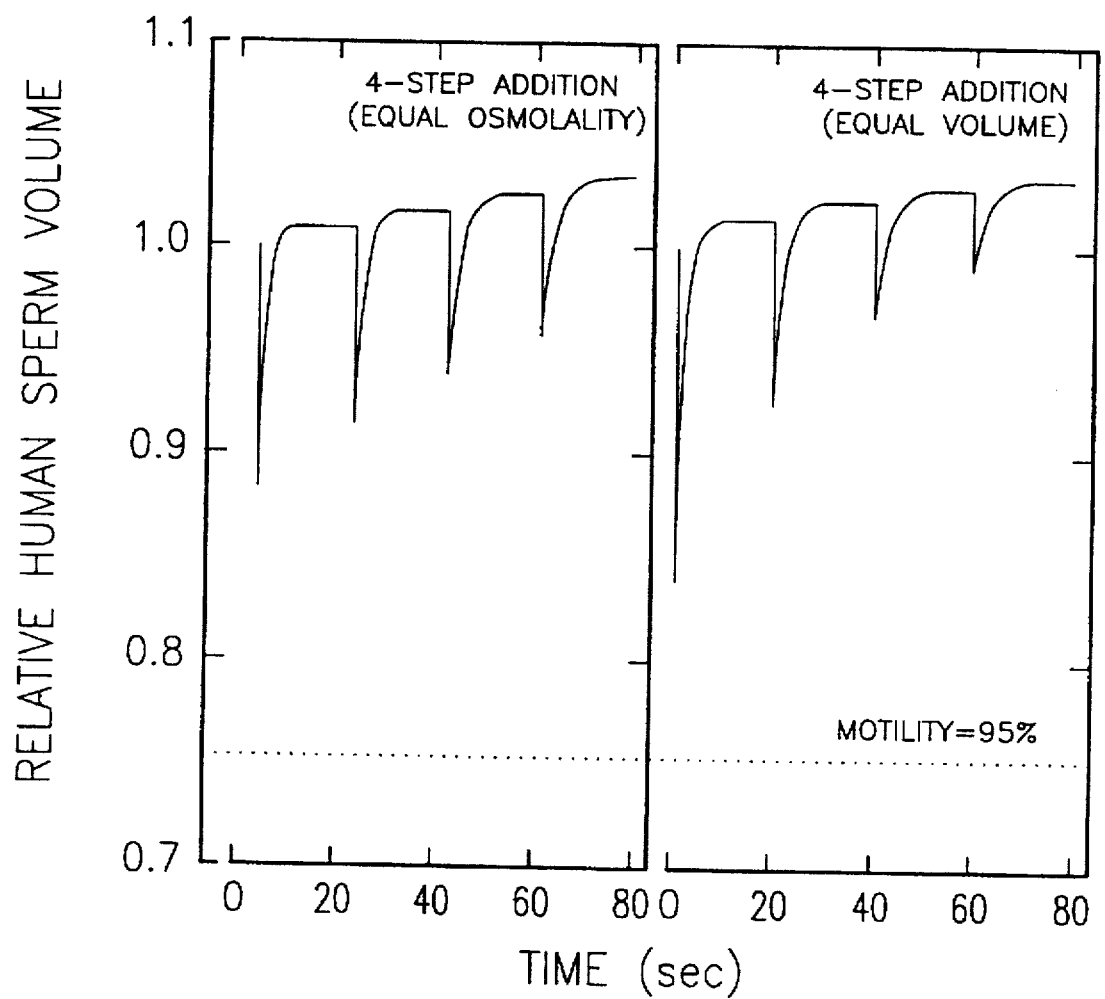

Referring to FIG. 11, there is shown a comparison between a four-step FVS addition of glycerol and a four-step FMS of glycerol.

From FIGS. 9 to 11, a one-step addition of glycerol to sperm is predicted to cause a 10% to 20% sperm motility loss. This loss is predicted to occur because the minimum volume which the sperm can attain during this addition is approximately 72% of the original cell volume, a value less than the minimumly acceptable LVL of 75% previously determined above. In contrast, a four-step FVS or FMS addition of glycerol was predicted to greatly reduce such sperm motility loss (less than 5%).

Figure 12:
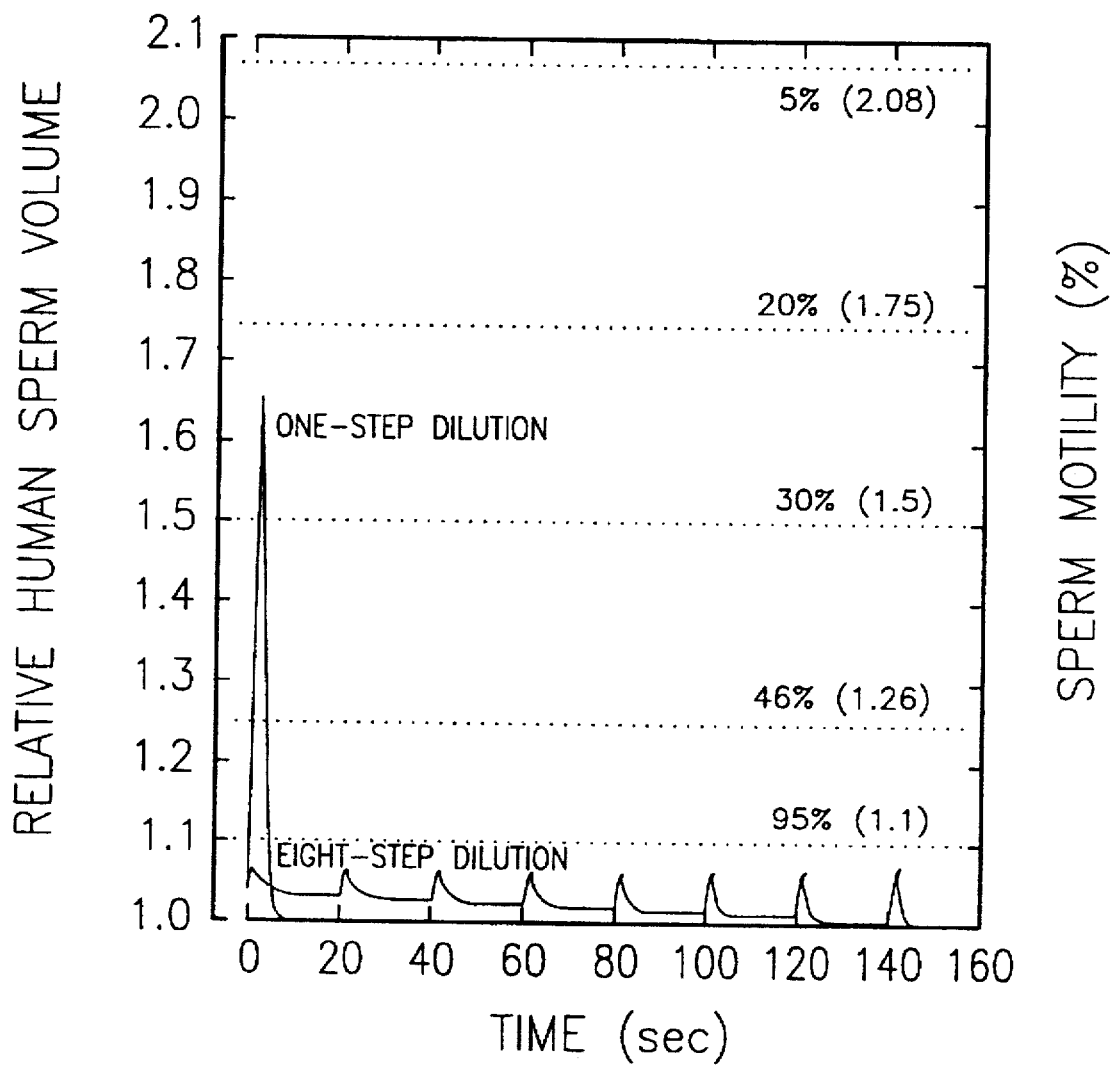

Referring to FIG. 12, there is shown a one-step removal of glycerol. This removal was predicted to cause as high as 70% motility loss because the maximum cell volume during the glycerol removal was calculated to be over 1.6 times larger than the isotonic cell volume, much higher than the upper volume limit of the sperm.

Figure 13:
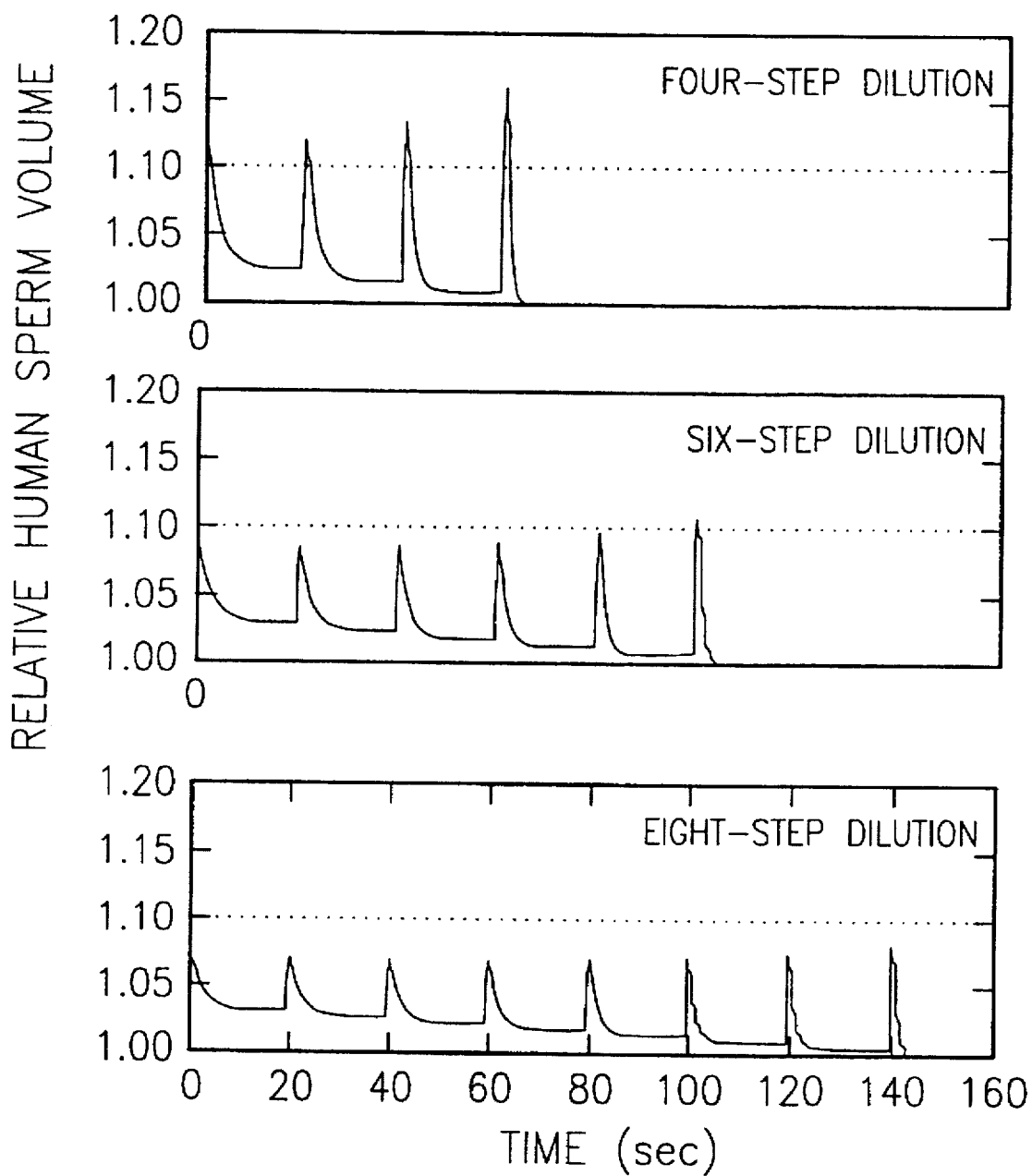

Referring to FIG. 13, there is shown a four-step, a six-step, and an eight-step FMS removal procedure. The four-step and six-step procedures were predicted to significantly reduce the sperm motility loss but still may cause over a 5% motility loss. An eight-step FMS removal was predicted to prevent sperm motility loss below the 5% level.

Figure 14:
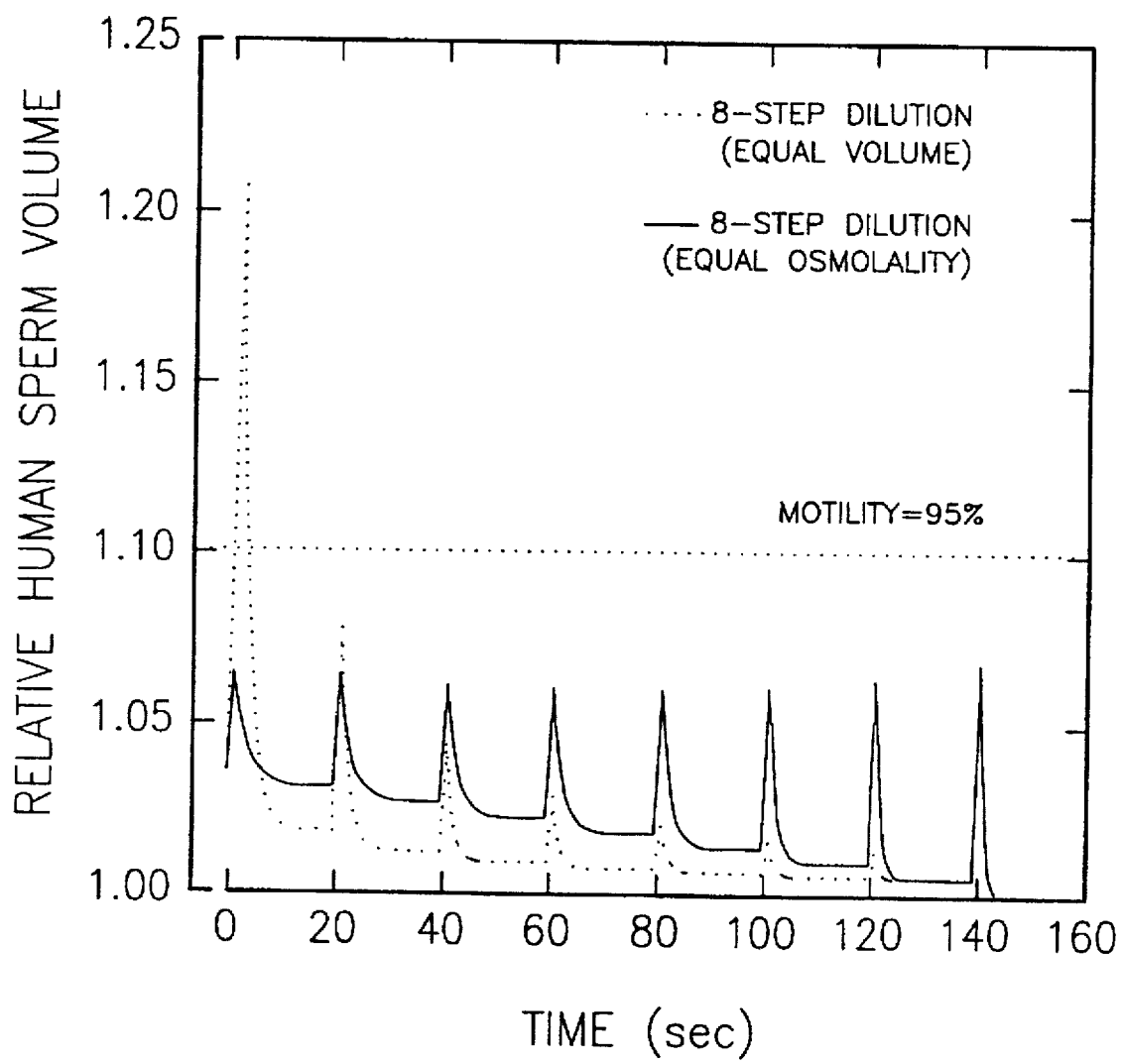

Referring to FIG. 14, there is shown a comparison between the eight-step FMS and the eight-step FVS removal procedures. The eight-step FMS removal was predicted to prevent sperm motility loss over the FVS procedure. An eight-step FVS removal was predicted to cause a maximum cell swelling of over 1.2 times higher than isotonic cell volume while FMS removal was predicted to be much lower than the UVL, indicating that the eight-step FVS removal is not as good as eight-step FMS removal. Also apparent from the computer simulation was the prediction that the human sperm would rapidly achieve an osmotic equilibrium (within seconds) during the 1-step or stepwise glycerol addition or removal. This further indicated that only a short time interval between steps of glycerol addition or removal was required.

In sum, a four-step FMS addition and an eight-step FMS removal of glycerol were predicted to be optimal protocols to prevent sperm motility loss in human sperm using the foregoing equations.

Figure 15:
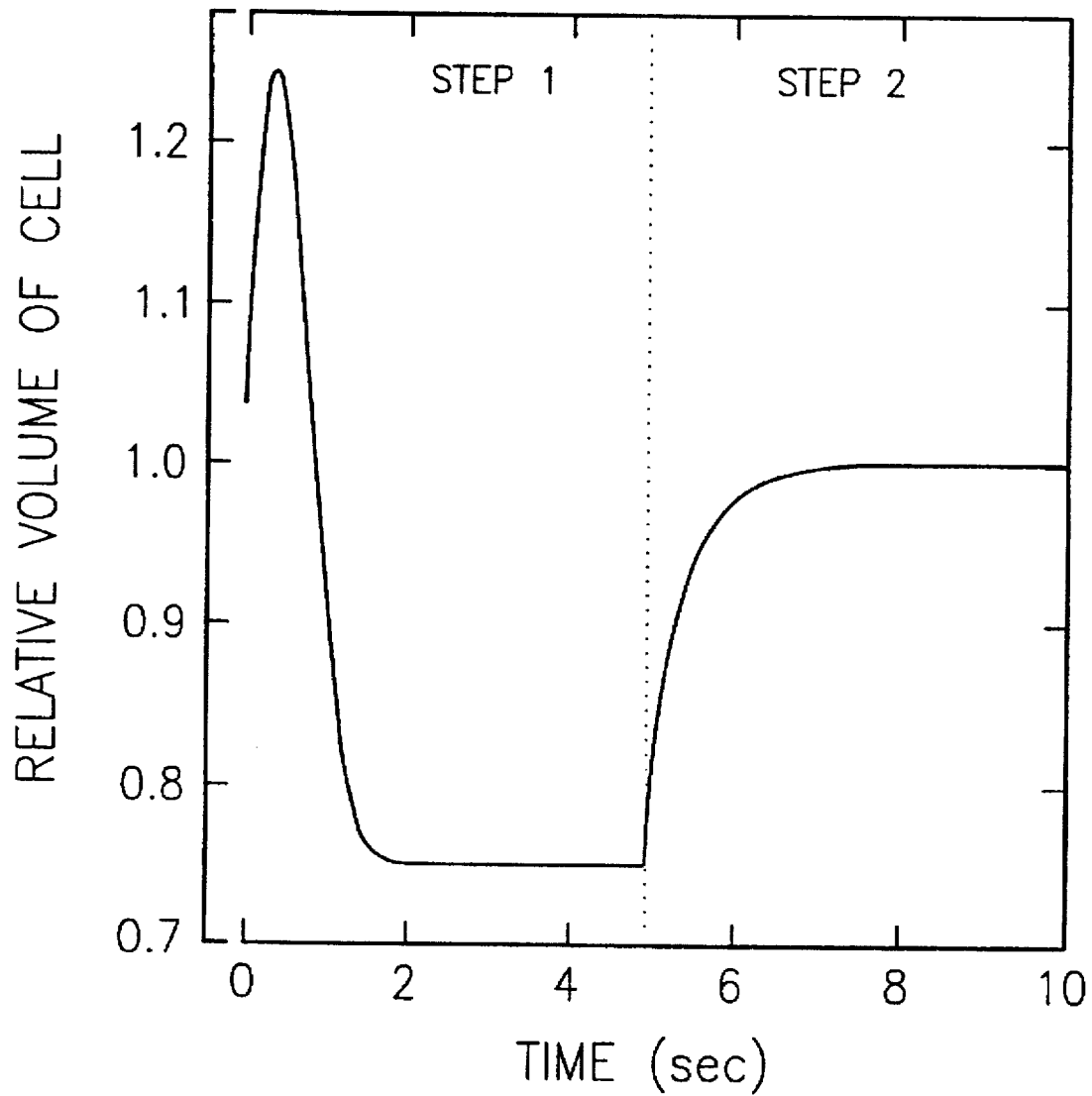
FIG. 15 is a graphical portrayal of an example of sperm cell volume change over time during a two-step removal of a cryoprotectant.

A two-step removal of CPA from the cells using a nonpermeating solute as an osmotic buffer has been previously used to avoid the osmotic injury to other cell-types. The detailed procedure is: (1) the CPA is directly removed from the cells by transferring cells to a hyperosmotic medium (osmotic buffer) containing no CPA but only non-permeating solutes, and then (2) the cells are directly transferred to an isotonic solution. It has been known that 600 mOsm is the hyperosmotic upper tolerance limit for human sperm (FIG. 9). Therefore, osmolality of the osmotic buffer medium should not be over 600 mOsm. Under this limit, a hyperosmolality of 600 mOsm is expected to provide the maximum "buffer effect" to reduce the sperm volume swelling during the first step of the "two-step" procedure for glycerol removal. Sperm volume change during the 2-step glycerol (1M) removal process using a 600 mOsm buffer medium was calculated and shown in FIG. 15. It was predicted that maximum volume the sperm would achieve 1.25 times of the isotonic cell volume, which is higher than the UVL of the sperm, and might cause over 50% sperm motility loss.

Example 3

Examination of the Osmotic Injury Actually Found Using a Previously Modeled CPA Addition or Removal Procedures TL-HEPES medium with 2M glycerol was either one-step or stepwise added to an equal volume of the isotonic sperm suspension to achieve a final 1M glycerol concentration at 22° C. Glycerol in the sperm was removed by dilution either by a one-step or stepwise addition of the TL-HEPES medium with or without an osmotic buffer (sucrose) placed into the cell suspension. The detailed procedures for the glycerol addition and removal are described in Tables 2–5. Sperm motility before, during, and after the different glycerol addition and removal procedures was measured by CASA. The membrane integrity of the sperm was determined by the dual staining technique and flow cytometry.

TABLE 2

Procedures used in 4-step addition of 1 ml of 2 M glycerol solution of 1 ml of isotonic sperm suspension.

| FVS | FMS |
|---|---|
| Add 0.25 ml of 2 M glycerol 4 times to 1 ml isotonic sperm suspension | Stepwise add 0.14, 0.19, 0.27 and 0.4 ml of 2 M glycerol to isotonic sperm suspension |

The time interval between two steps was approximately 1–2 minutes. The volume of solution added in each step was calculated using Equations 5 or 6.

TABLE 3

Procedures used in 1-step and 8-step removal of 1 M glycerol from the human sperm
8-Step Dilution

| FVS | FMS |
|---|---|
| Add 100 µl of isotonic TALP 7 times to sperm suspension to achieve a final glycerol concentration, 0.125 M. After centrifugation, 710 µl of supernatant was taken off. Remaining cell suspension volume is 90 µl | Stepwise add 14.3, 19, 26.6, and 40 µl of isotonic TALP medium to 100 µl of sperm suspension with 1 M glycerol; (2) centrifuge the cell suspension at 400 g for 5–7 minutes.; (3) take off 170 µl of the supernatant; Stepwise add 10, 20 and 60 µl of isotonic solution to the remaining 30 ul of sperm suspension. After the above 7 steps dilution, the glycerol concentration in the sperm suspension is 0.125 M. The final suspension volume is 90 µl |

The final 90 µl of sperm suspension were further diluted by adding 180 µl of TALP solution for the CASA analysis. The time interval between two steps is approximately 1–2 minutes. The volume of diluent added in each step was calculated using Equations 7 or 8.

One Step Dilution

Add 2000 µl of isotonic solution directly to 100 µl of cell suspension with 1M glycerol.

Table 4. Procedures used in 2-step removal of 1M glycerol from the human sperm using sucrose as an osmotic buffer (1) Add 2000 µl of sucrose buffer medium (TALP+ sucrose, 600 mOsm) to 100 µl of sperm suspension with 1M glycerol; (2) centrifuge the suspension (400 g for 7 minutes) and take off the supernatant; and (3) resuspend cell pellet with 500 ul isotonic TALP medium.

Results from Experimental Examination

Figure 16:
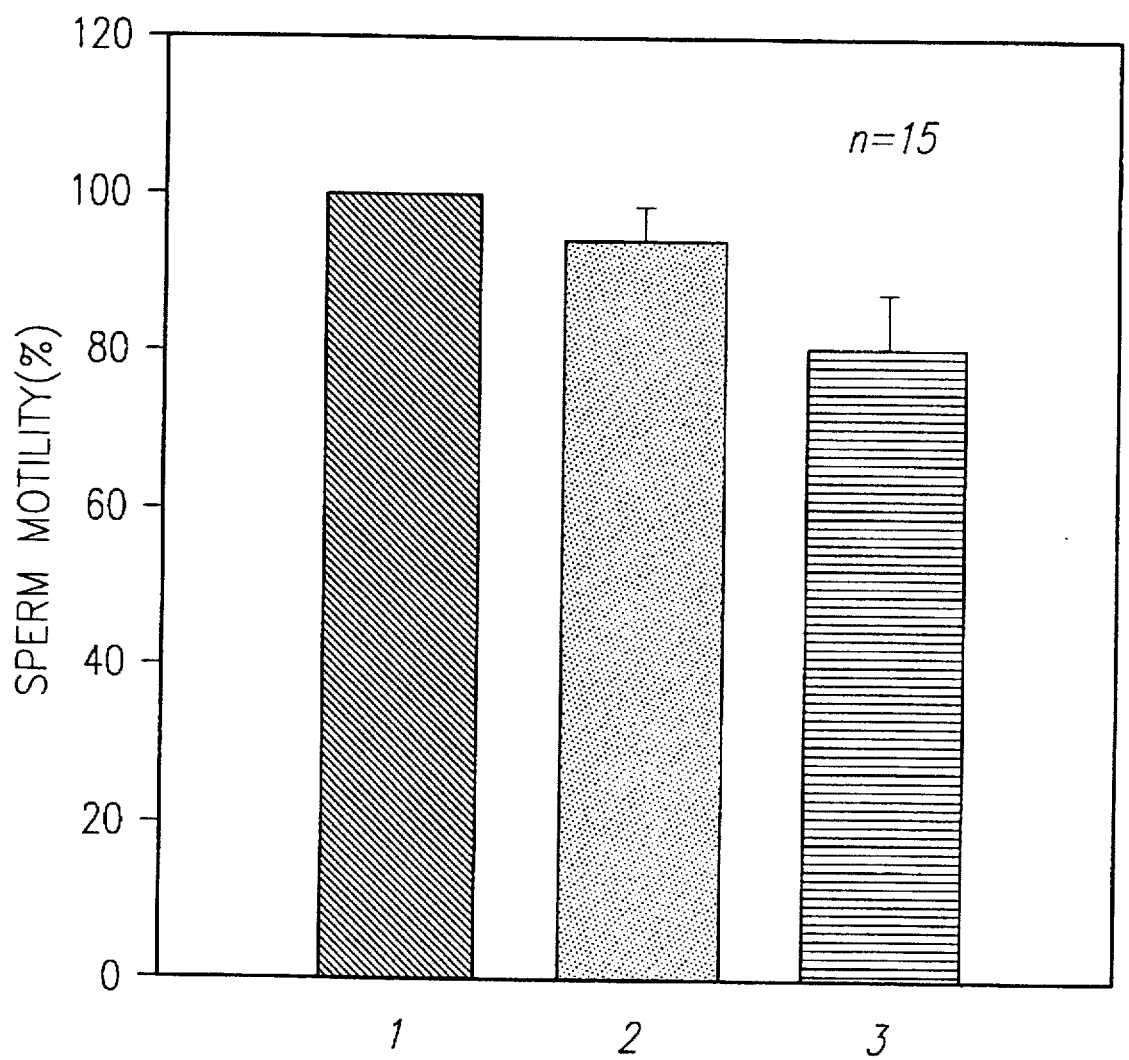
FIGS. 16 to 18 are graphical portrayals of examples comparing injury to sperm cells using various schemes of cryoprotectant addition or removal.
Figure 17:
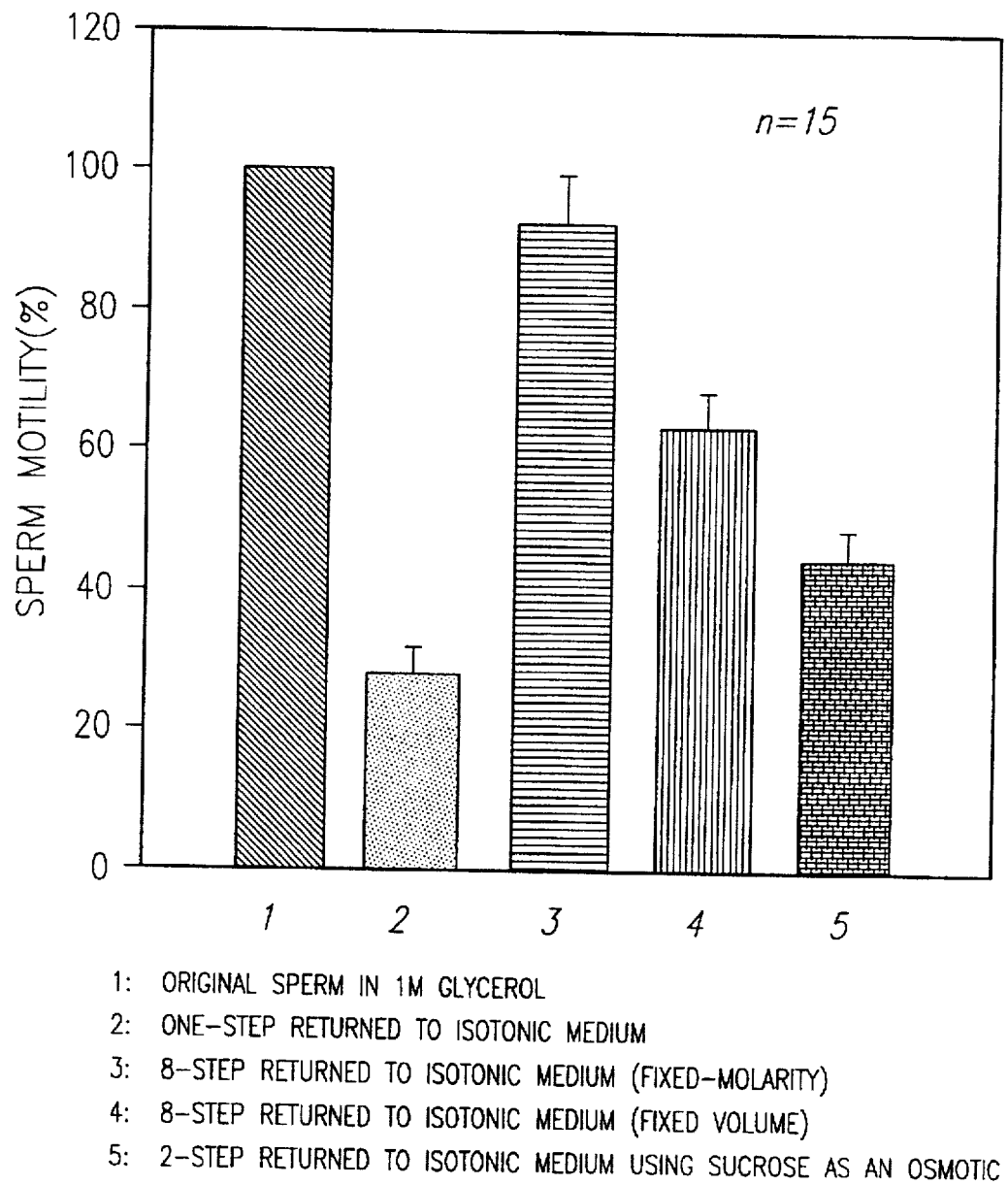

Glycerol was experimentally added to or removed from the human sperm using the stepwise procedures as predicted from the computer simulation. Percent motility of the human sperm after one step or a four-step FMS addition of glycerol (Table 2) is shown in FIG. 16. One step addition created approximately 20% sperm motility loss while the four-step addition, less than 8%. FIG. 17 shows effects of different glycerol removal procedures (Table 3) on the human sperm motility loss. Less than 30% motile sperm kept motility after one-step removal of glycerol while majority of sperm (over 92%) maintained the motility after the eight-step FMS removal. The motility loss caused by a two-step removal of glycerol using sucrose as a non-permeating buffer (total osmolality of the buffer medium was 600 mOsm) was close to 45%. Thirty-five percent of the sperm lost motility after a eight-step FVS removal of glycerol. The experimental results agree well with the predictions generated from computer simulation.

Figure 18:
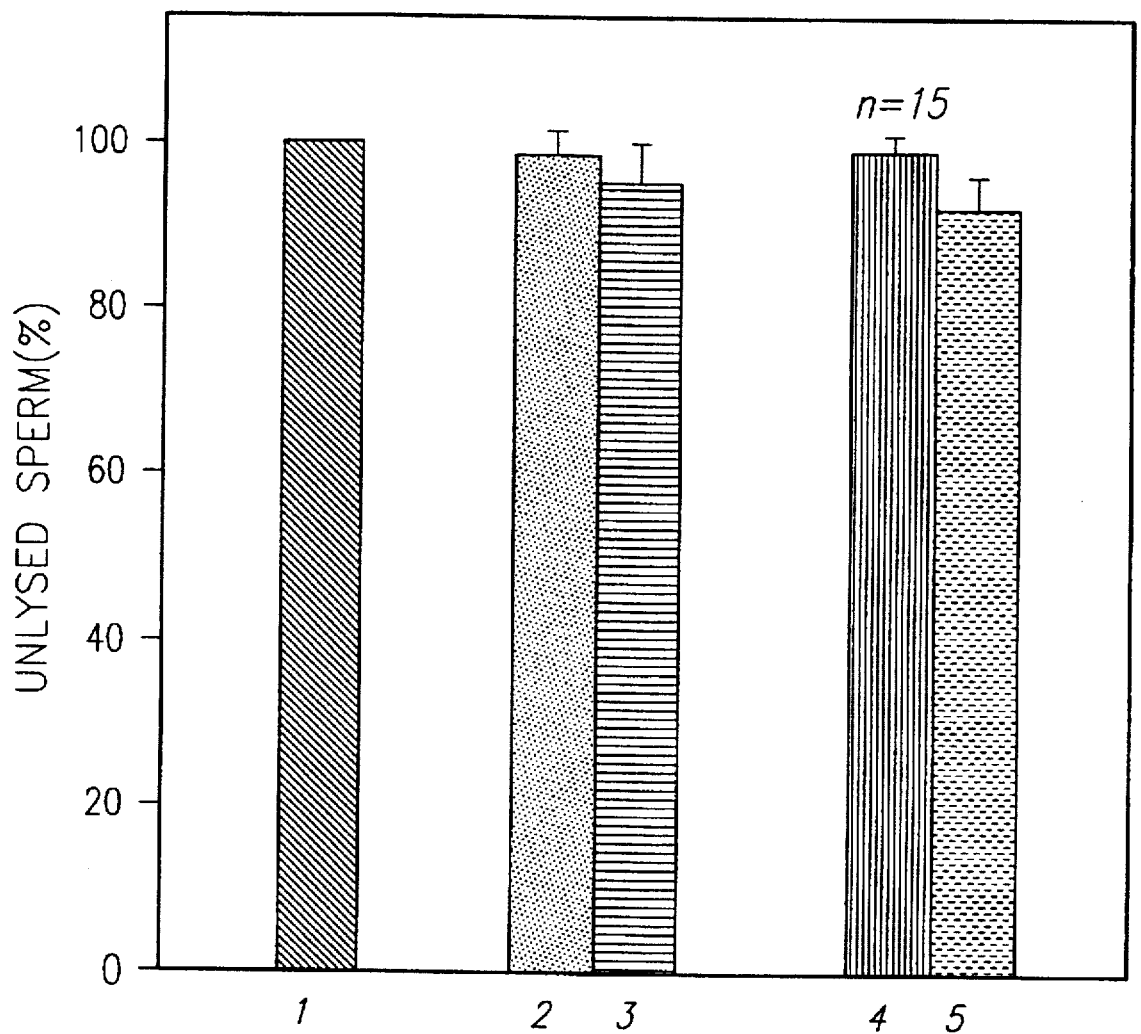

FIG. 18 shows the membrane integrity of the human sperm in 1M glycerol solution or after addition and removal of 1M glycerol by the different procedures. The sperm appeared to maintain membrane integrity under all experimental conditions.

DISCUSSION

The addition of CPA to the sperm before cooling and its removal from sperm after warming are two of very important procedures in sperm cryopreservation. The present invention offers a new methodology to define optimal procedures to carry out either or both of these procedures in a fashion to reduce osmotic injury of the sperm. The calculated procedures were implemented and the results agree remarkably well with prediction.

This example presented two CPA addition or removal schemes (FVS and FMS). As the example shows, the Fixed-Molarity-Step is preferable to reduce osmotic injury over the Fixed-Volume-Step. In particular, for human sperm, the example shows that a four-step FMS addition of glycerol to the sperm and an eight-step FMS removal of glycerol from the sperm were predicted to be optimal, which was confirmed upon implementation. Upon reviewing each scheme, the minimum/maximum cell volumes after each step of FVS addition/removal was uneven or unequal, some of which exceeded the LVL and UVL of the sperm. In contrast, minimum/maximum cell volumes after each step of FMS addition/removal of glycerol were shown to be relative even (FIGS. 11 and 14). For a fixed number of steps, the extent of cell volume change during CPA addition/removal using the FMS scheme is much smaller than that using the FVS scheme (also see FIGS. 11 and 14).

A careful review of the foregoing methodology demonstrates that in the preferred practice of this invention, the sperm cell volume change will be kept in a range which the sperm cells can tolerate during the addition or removal of the cryoprotective agent. For an example, a preferred method to remove cryoprotectant would swell the sperm cells to at least 90% of the upper volume limit (i.e. 0.9 times the upper volume limit) but not substantially exceed the upper cellular volume limit. For another example, a preferred method to add cryoprotectant would shrink the sperm cells to at least 110% of the lower volume limit (i.e. 1.1 times the lower volume limit) but not substantially drop below the lower cellular volume limit. However, the total number of steps for the addition/removal and the time required for completing the addition/removal are also important because of potential chemical toxicity CPA can have upon unfrozen sperm. Generally speaking, CPA should be added into or removed from sperm as soon as possible before cooling or after warming to eliminate long periods of exposure to CPA at relatively high temperatures. Any action to limit such exposure requires the least number of steps for the addition or removal of the CPA. Thus, this is a second feature for developing an optimal procedure for the addition/removal of CPA.

Accordingly, the preferred stepwise procedure for CPA addition/removal will (1) keep sperm cell volume in an accepted range and (2) reduce the total number of steps required to add/remove the CPA. To achieve this goal, the following two criteria can be taken into account in computer simulation to predict the optimal procedures: (a) the maximum/minimum cell volume during each step of CPA addition/removal must be constant and (b) the maximum/minimum cell volume must be close to (not exceed) the UVL and LVL of the sperm cells. Although the FMS scheme is shown in the foregoing examples to be better than the FVS, it still did not completely satisfy the criterion (a) (see FIGS. 11 and 14). Using computer simulation, a practitioner in the art can use the information in this specification to further customize a protocol specifically for their needs, e.g. better satisfy both criteria (a) and (b).

An important step to practice this invention is to determine the osmotic tolerance of the sperm cells. However, these limits are effected by the assays used to evaluate sperm viability. For example, see Example I, sperm motility was used as a standard of sperm viability because of relatively high sensitivity of the sperm motility to the osmotic change and the requirement of sperm motility for most clinical applications. Other characteristics of sperm may be similarly used to determine appropriate protocols, which may offer different osmotic tolerance limits.

Finally, it should be remembered that the effect of potential chemical toxicity of CPA on sperm cell viability is another reason causing sperm cell injury during the addition and removal of CPA for sperm cell cryopreservation. Given a CPA type and CPA concentration, it is generally accepted that the potential toxicity of the CPA to the cells is decreased with a decrease of cell exposure time to the CPA and a decrease in temperature.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

We claim:

1. A method to add cryoprotectant to the sperm cells of an animal species comprising:
    a) predetermining a lower cellular volume limit below which a user-defined fraction of sperm cells lose their viability,
    b) selecting a first concentration of cryoprotectant solution,
    c) calculating whether said first concentration of cryoprotectant solution will cause the sperm cells to shrink below the lower cellular volume limit by a calculation which uses the water permeability coefficient and the cryoprotectant permeability coefficient of the sperm cells, repeating steps b) and c) as necessary in order to calculate a predetermined concentration of cryoprotectant solution which will permit increasing of the concentration of cryoprotectant in the sperm cells while still maintaining the viability of a user-defined fraction of the sperm cells,
    d) contacting said sperm cells with the solution of the predetermined concentration of cryoprotectant.

2. The method of claim 1, wherein steps (b) and, (c) and (d) are repeated for a second concentration of cryoprotectant that is less dilute than said first concentration.

3. The method of claim 1, wherein said lower cellular volume limit is predetermined by shrinking the sperm cells of said animal species in increasingly hypertonic conditions until a predetermined fraction of the sperm cells lose their viability.

4. The method of claim 1, wherein said cryoprotectant comprises glycerol.

5. The method of claim 1, wherein said contacting comprises contacting said sperm cells with the cryoprotectant solution in two or more substantially constant volumes.

6. The method of claim 1, wherein said contacting comprises contacting said sperm cells with the cryoprotectant solution in two or more volumes wherein said volumes increase the level of cryoprotectant in the sperm cells by substantially constant increments in molarity.

7. The method of claim 1, wherein said lower cellular volume limit is about 75% of the isotonic volume of the sperm cells.

8. The method of claim 1, wherein said viability is measured by analysis of sperm motility.

9. The method of claim 1, wherein said concentration of each aliquot shrinks the sperm cells to a volume that is between said lower cellular volume limit and 110% of said lower cellular volume limit.

10. The method of claim 1, wherein said lower cellular volume limit is based upon the sperm cells' ability to fertilize.

11. A method to add cryoprotectant to sperm cells of an animal species, comprising:

contacting said sperm cells with one or more stepwise additions of aliquots containing said cryoprotectant, wherein each aliquot has a predetermined concentration of said cryoprotectant that is higher than the cryoprotectant concentration within the sperm cells with which it is contacted, said predetermined concentration substantially preventing the volumetric excursion of said sperm cells beyond a predetermined lower cellular volume limit, and said predetermined concentration being predetermined by determining the cellular volume of said sperm cells for a given concentration of said cryoprotectant with differential equations:

$$J_v = 1/A_c \, dV(t)/dt$$
$$= -L_p\{(C_{salt}^e - C_{salt}^i) + \sigma(C_{CPA}^e - C_{CPA}^i)\}$$

$$J_{CPA} = 1/A_c \, dN_{CPA}/dt$$
$$= \bar{C}_{CPA}(1-\sigma)J_v + P_{CPA}(C_{CPA}^e - C_{CPA}^i)RT$$

$$C_{salt}^i(t) = C_{salt}^{e,o}\{(V(0) - V_b - \bar{V}_{CPA}N_{CPA}^{i,o})/(V(t) - V_b - \bar{V}_{CPA}N_{CPA}^i(t))\}$$

$$C_{CPA}^i(t) = [N_{CPA}^i(t)]/[V(t) - V_b - \bar{V}_{CPA}N_{CPA}^i(t)]$$

wherein $J_v$=total volume flux, V=cell volume, t=time, N=mole number of the solute, A=cell surface area, $L_p$=water permeability coefficient, C=concentration of solute, $J_{CPA}$=cryoprotectant flux across the cell membrane, superscript e=extracellular, superscript i=intracellular, $\bar{C}_{CPA}$=average cryoprotectant concentration of extracellular and intracellular concentrations, R=gas constant, T=absolute temperature, $P_{CPA}$=cryoprotectant permeability coefficient of the sperm cell, $\sigma$=the reflection coefficient of said cryoprotectant, wherein $V_b$=osmotically-inactive cell volume, $\bar{V}_{CPA}$=partial mole volume of said cryoprotectant, 0=initial condition; and determining the size of said cellular volume relative to said predetermined lower cellular volume limit.

12. The method of claim 11, wherein said cryoprotectant is selected from the group consisting of dimethyl sulfoxide, glycerol, and ethylene glycol.

* * * * *

UNITED STATES PATENT AND TRADEMARK OFFICE
CERTIFICATE OF CORRECTION

PATENT NO. : 5,691,133
DATED : November 25, 1997
INVENTOR(S) : CRITSER, John K., et al.

It is certified that error appears in the above-identified patent and that said Letters Patent is hereby corrected as shown below:

On title page,

In Block 57 of the title page, line 6, please change "date" to -- data --.

In col. 4, line 48, please change "Sperm" to -- sperm --.

In col. 4, line 53, please change "Well" to -- well --.

In col. 7, line 36, please delete the period.

In col.10, line 29, please delete "the".

In col. 11, line 44, please insert --of-- after "volume".

In col. 16, line 11, please change "V " third occurrence, to $--\overline{V}--$.

In col. 16, line 12, please change "V " to $--\overline{V}--$.

In col. 16, line 16, please change "A" to $--A_c--$.

Signed and Sealed this

Sixteenth Day of June, 1998

Attest:

BRUCE LEHMAN

Attesting Officer        Commissioner of Patents and Trademarks